(12) United States Patent
Rinehart et al.

(10) Patent No.: US 6,316,214 B1
(45) Date of Patent: Nov. 13, 2001

(54) ETM-775 METABOLITE OF ECTEINASCIDIN 743

(75) Inventors: Kenneth L. Rinehart; Jose J. Morales, both of Urbana, IL (US); Joel Reid, Rochester, MN (US); Isabel Reymundo, Madrid (ES); Pablo Floriano, Madrid (ES); Lola Garcia Gravalos, Madrid (ES)

(73) Assignee: The Board of Trustees of the University of Illinois, Champaign, IL (US)

( * ) Notice: Subject to any disclaimer, the term of this patent is extended or adjusted under 35 U.S.C. 154(b) by 0 days.

(21) Appl. No.: 09/309,947

(22) Filed: May 11, 1999

Related U.S. Application Data

(60) Provisional application No. 60/085,024, filed on May 11, 1998.

(51) Int. Cl.[7] .................................................. C12Q 1/26
(52) U.S. Cl. ............................ 435/25; 514/250; 544/233
(58) Field of Search ............................ 435/25; 514/250; 544/233

(56) References Cited

U.S. PATENT DOCUMENTS

| | | | |
|---|---|---|---|
| 4,273,773 | 6/1981 | Demerson et al. | 424/250 |
| 5,089,273 | 2/1992 | Rinehart et al. | 424/520 |
| 5,256,663 | * 10/1993 | Rinehart et al. | 514/250 |
| 5,459,141 | 10/1995 | Vertesy et al. | 514/250 |
| 5,484,717 | 1/1996 | Zaccardi | 435/119 |
| 5,654,426 | * 8/1997 | Rinehart et al. | 540/466 |
| 5,721,362 | * 2/1998 | Corey et al. | 540/466 |
| 5,985,876 | * 11/1999 | Rinehart et al. | 514/250 |

FOREIGN PATENT DOCUMENTS

WO/9846080   10/1998   (WO).

* cited by examiner

Primary Examiner—Ralph Gitomer
(74) Attorney, Agent, or Firm—Ernest V. Linek; Banner & Witcoff, Ltd.

(57) ABSTRACT

The purification and structure elucidation of several products of the metabolism of Et 743 by human cytochrome CYP3A4 have been accomplished. These compounds are abbreviated herein as "ETM" followed by a numeric value, which represents the approximate molecular weight. Three compounds have been identified to date, namely ETM 305, ETM 775 and ETM 204. The structures of these ecteinascidin metabolites are as follows:

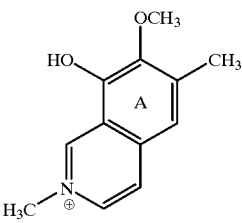

ETM 204

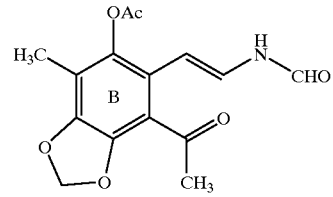

ETM 305

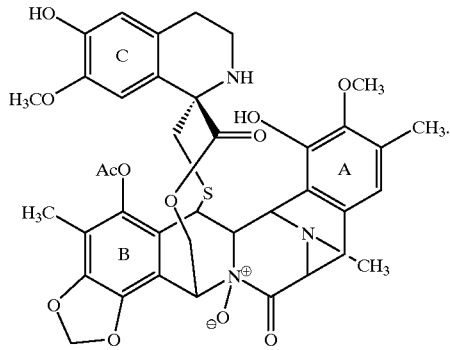

ETM 775

2 Claims, 25 Drawing Sheets

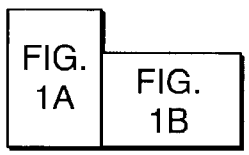

FIG. 1

MORALES, KLR, ETH-SIOH-1 IN CDC13

EXPL   S3PUL

| SAMPLE | | DEC. & VT | |
|---|---|---|---|
| DATE | FEB 27 98 | DFRQ | 499.699 |
| SOLVENT | CDC 13 | DN | HL |
| FILE | EXP | DPWR | 20 |
| ACQUISITION | | DOF | 6 |
| STFRQ | 499.699 | DM | NNN |
| TN | 111 | DMM | C |
| AT | 3.277 | DMF | 200 |
| NP | 39296 | DSEQ | |
| SW | 5996.1 | DRES | 1.0 |
| FB | 3400 | HOMO | N |
| BS | 16 | DEC2 | |
| TPWR | 63 | DFRQ2 | 0 |
| PW | 4.7 | DN2 | |
| DL | 0 | DPWR2 | 1 |
| TOF | 0 | DOF2 | 0 |
| NL | 400 | DM2 | N |
| CT | 160 | DMM2 | C |
| ALOCK | N | DMF2 | 200 |
| GAIN | NOT USED | DSEQ2 | |
| FLAGS | | DRES2 | 1.0 |
| 11 | N | HOMO2 | N |
| LN | N | PROCESSING | |
| DP | Y | 16 | 6.30 |
| HS | NN | WTFILE | |
| DISPLAY | | PROC | FT |
| SP | -138.2 | FN | NOT USED |
| WP | 5133.1 | MATH | R |
| V$ | 8848 | | |
| SC | 0 | WERR | |
| WC | 250 | WEXP | |
| NIMM | 20.53 | WBS | |
| LS | 33.57 | WNT | |
| RFL | 4131.0 | | |
| RFP | 3627.8 | | |
| TH | 7 | | |
| INS | 1.000 | | |
| NM   PH | | | |

FIG. 1A

HPLC CHROMATOGRAM OF ETM-SiOH-3 (ETM 305)

ETM 305

HPLC CONDITIONS

COLUMN: Phenomenex/Ultracarb 5 ODS. ID 150 x 10 mm
MOBILE PHASE: 3:1 MeOH/$H_2O$ 0.02 M NaCl
FLOW RATE: 1mL/min
DETECTOR: DAD

UV SPECTRUM OF ETM 775.

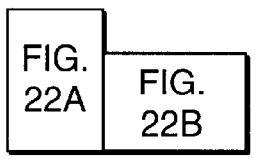

FIG. 22

MORALES, KLR, MZ IN CD3OD

EXPL    S2PUL

|  SAMPLE  |  | DEC. & VT |  |
|---|---|---|---|
| DATE | MAR 17 98 | DFRQ | 499.701 |
| SOLVENT | METHANOL | DN | H1 |
| FILE | EXP | DPWR | 20 |
| ACQUISITION |  | DOF | 0 |
| STFRQ | 499.701 | DM | NNN |
| TN | 111 | DMM | C |
| AT | 4.003 | DMF | 200 |
| NP | 48000 | DSEQ |  |
| SW | 5996.1 | DRES | 1.0 |
| FB | 3400 | HOMO | N |
| BS | 16 | DEC2 |  |
| TPWR | 63 | DFRQ2 | 0 |
| PW | 4.5 | DN2 |  |
| DL | 0 | DPWR2 | 1 |
| TOF | 0 | DOF2 | 0 |
| NT | 3000 | DM2 | N |
| CT | 1044 | DMM2 | C |
| ALOCK | N | DMF2 | 200 |
| GAIN | NOT USED | DSEQ2 |  |
| FLAGS |  | DRES2 | 1.0 |
| 11 | N | HOMO2 | N |
| LN | N | PROCESSING |  |
| DP | Y | LB | 0.30 |
| HS | NN | WTFILE |  |
| DISPLAY |  | PROC | FT |
| SP | -0.1 | FN | NOT USED |
| WP | 4997.0 | MATH | F |
| V$ | 31752 |  |  |
| SC | 0 | WERR |  |
| WC | 250 | WEXP |  |
| HZMM | 19.99 | WBS |  |
| LS | 33.57 | WNT |  |
| RFL | 2154.5 |  |  |
| RFP | 1649.0 |  |  |
| TH | 7 |  |  |
| INS | 1.000 |  |  |
| NM | PH |  |  |

FIG. 22A

ETM-775 METABOLITE OF ECTEINASCIDIN 743

CROSS-REFERENCE TO RELATED APPLICATION

This application claims priority benefit from copending U.S. Provisional Application Ser. No. 60/085,024, filed May 11, 1998, the disclosure of which is hereby incorporated herein by reference.

BACKGROUND OF THE INVENTION

The ecteinascidins (herein abbreviated Et or Et's) are exceedingly potent antitumor agents isolated from the marine tunicate *Ecteinascidia turbinata*. In particular, Et's 729, 743 and 722 have demonstrated promising efficacy in vivo, including activity against P388 murine leukemia, B16 melanoma, Lewis lung carcinoma, and several human tumor xenograft models in mice.

The isolation and characterization of natural Et 743 is taught in U.S. Pat. No. 5,089,273 which is hereby incorporated herein by reference. The preparation of synthetic Et 743 is taught in U.S. Pat. No. 5,721,362, which is hereby incorporated herein by reference.

The antitumor activities of ecteinascidin compounds, particularly Et 729 and Et 743 are well documented in the scientific literature. See for example, Goldwasser et al., *Proceedings of the American Association for Cancer Research*, 39: 598 (1998); Kuffel et al., *Proceedings of the American Association for Cancer Research*, 38: 596 (1997); Moore et al., *Proceedings of the American Association for Cancer Research*, 38: 314 (1997); Mirsalis et al., *Proceedings of the American Association for Cancer Research*, 38: 309 (1997); Reid et al., *Cancer Chemotherapy and Pharmacology*, 38: 329–334 (1996); Faircloth et al., *European Journal of Cancer*, 32A, Supp. 1, pp. S5 (1996); Garcia-Rocha et al., *British Journal of Cancer*, 73: 875–883 (1996); Eckhardt et al., *Proceedings of the American Association for Cancer Research*, 37: 409 (1996); Hendriks et al., *Proceedings of the American Association for Cancer Research*, 37: 389 (1996); the disclosures of which are hereby incorporated herein by reference.

Ecteinascidin 743 (Et 743) has the following structure:

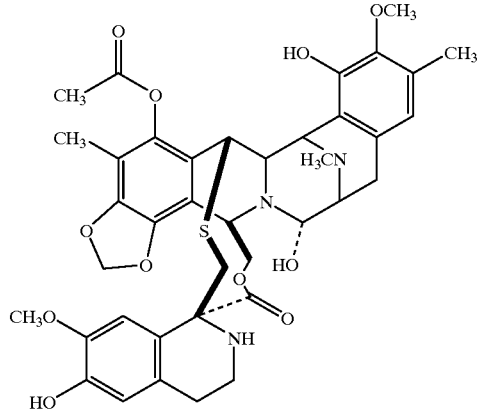

Et 743

In view of the impressive antitumor activities of this class of compounds, the search continues for related structures that may possess equal or higher levels of antitumor activity. The present invention, which is directed to the isolation and characterization of natural metabolites of Et 743, is a result of these continued studies.

SUMMARY OF THE INVENTION

The purification and structure elucidation of several products of the metabolism of Et 743 by human cytochrome CYP3A4 have been accomplished. These compounds are abbreviated herein as "ETM" followed by a numeric value which represents the approximate molecular weight.

For example, ETM 305 and ETM 775 were isolated from a metabolic mixture obtained from a biochemical study performed by the Analytical Chemistry Department at PharmaMar, Spain. A similar metabolic study carried out by the Mayo Clinic led to the identification of ETM 204. The structures of these ecteinascidin metabolites are as follows:

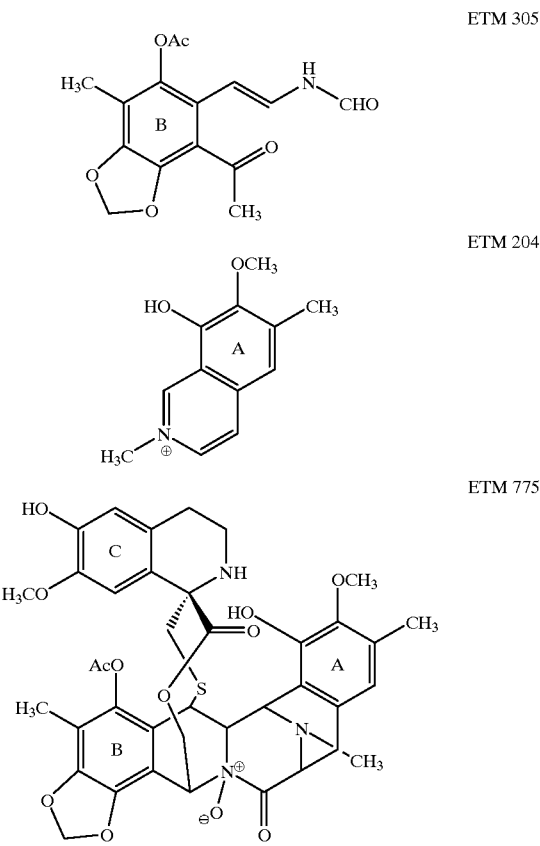

ETM 305

ETM 204

ETM 775

BRIEF DESCRIPTION OF THE DRAWINGS

The present invention may be better understood by reference to the drawings accompanying this specification, wherein.

DETAILED DESCRIPTION OF THE INVENTION

I. Et 743 Metabolic Study

A. Preparation of Metabolic Mixture—ETM

Et-743 (50 μM) was incubated with 0.4 mg/ml of human lymphoblast-expressed CYP3A4 isoform (Gentest Corporation, Woburn, Mass.) in 0.1 M Tris-HCl buffer (pH 7.4) containing an NADPH generating system (0.4 mM NADP$^+$, 25 mM glucose-6-phosphate, 0.5 U/ml glucose-6-phosphate dehydrogenase and 3.3 mM magnesium chloride). After four (4) hours at 37° C., the reaction was stopped with ice cold acetonitrile and the solids removed by centrifugation (12,000 g, 4 min.). Supernatants were analyzed by HPLC.

B. Purification of ETM 305 and ETM 775

Figure 1B:
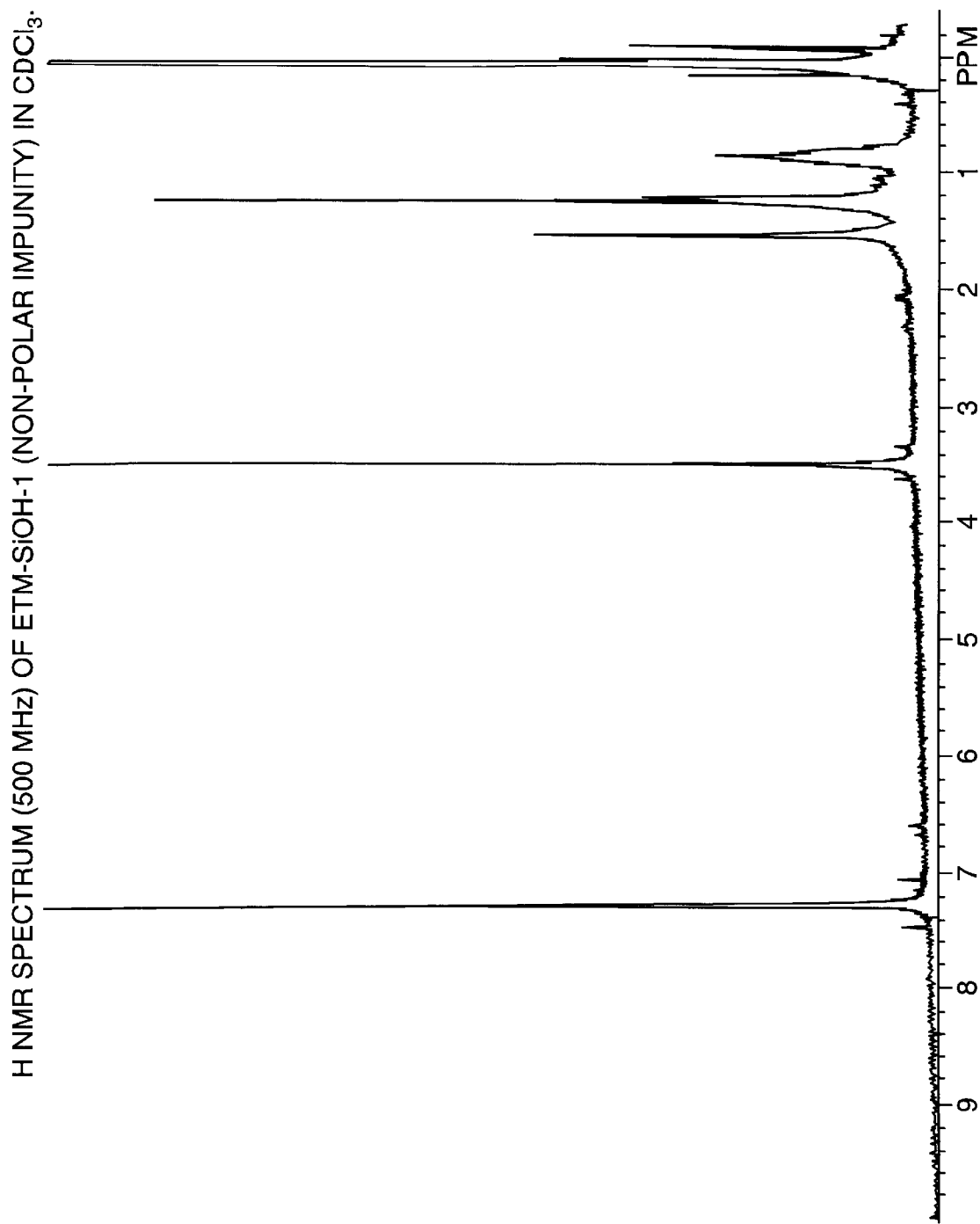
FIG. 1 is the $^1$H NMR spectrum (500 MHz) of ETM-SiOH-1 (non-polar impurity) in $CDCl_3$.

2.6 mg of ETM (generated as in A, above) was dissolved in a small amount of CHCl$_3$ and loaded into a silica gel column (8×100 mm glass column filled with a silica gel/CHCl$_3$ slurry). First, the column was eluted with CHCl$_3$ followed by CHCl$_3$/MeOH mixtures (98, 96, 94, 92 and 90%). A total of ten test tubes were collected (3 mL each) and combined on the basis of TLC to yield four fractions (Table 1). The less polar and non-cytotoxic fraction (ETM-SiOH-1, 2 mg) consisted of a lipid not structurally related to Et 743 as revealed by the $^1$H NMR spectrum (FIG. 1).

Figure 2:
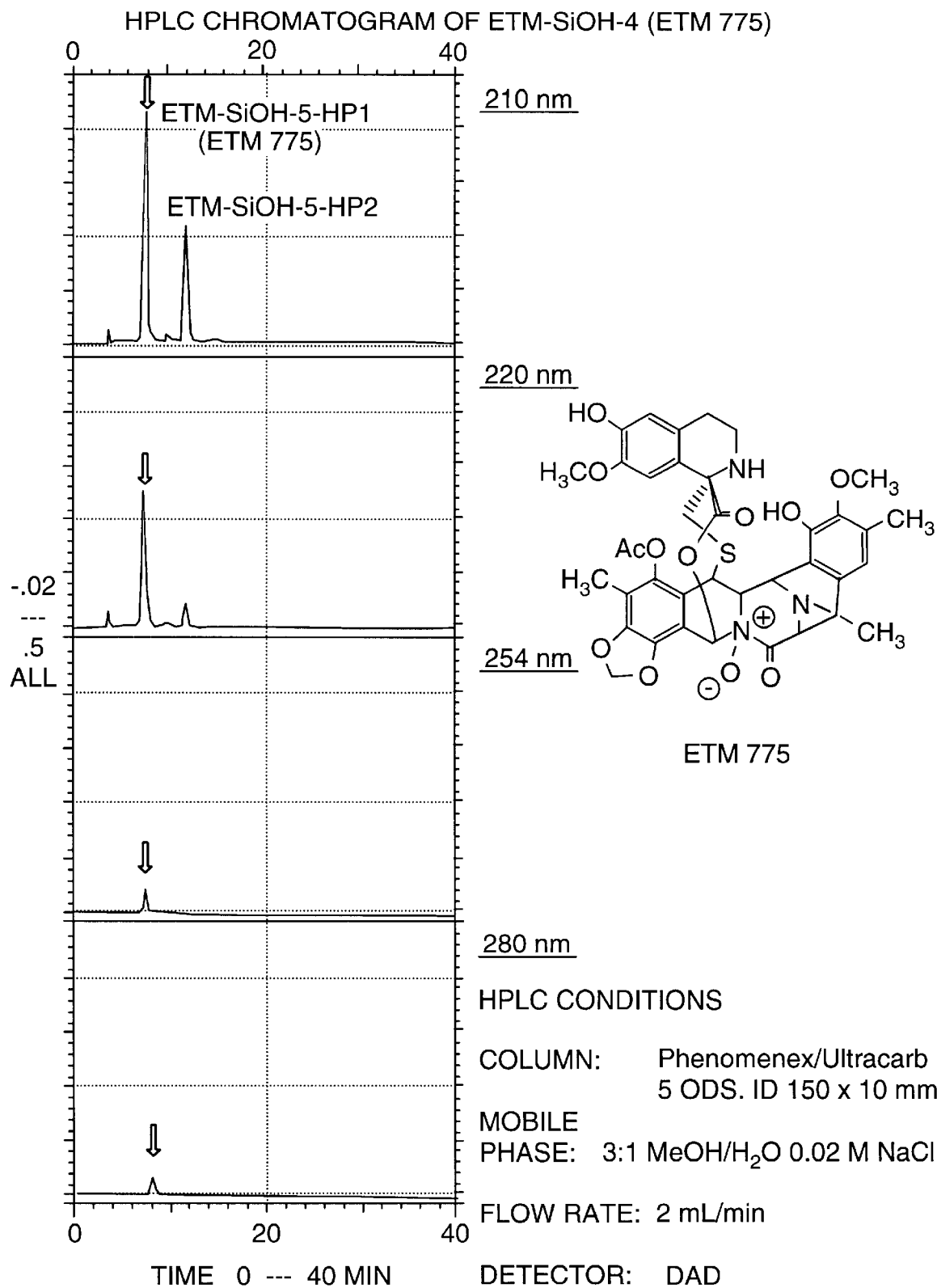
FIG. 2 is the HPLC chromatogram of ETM-SiOH-4 (ETM 775)
Figure 3:
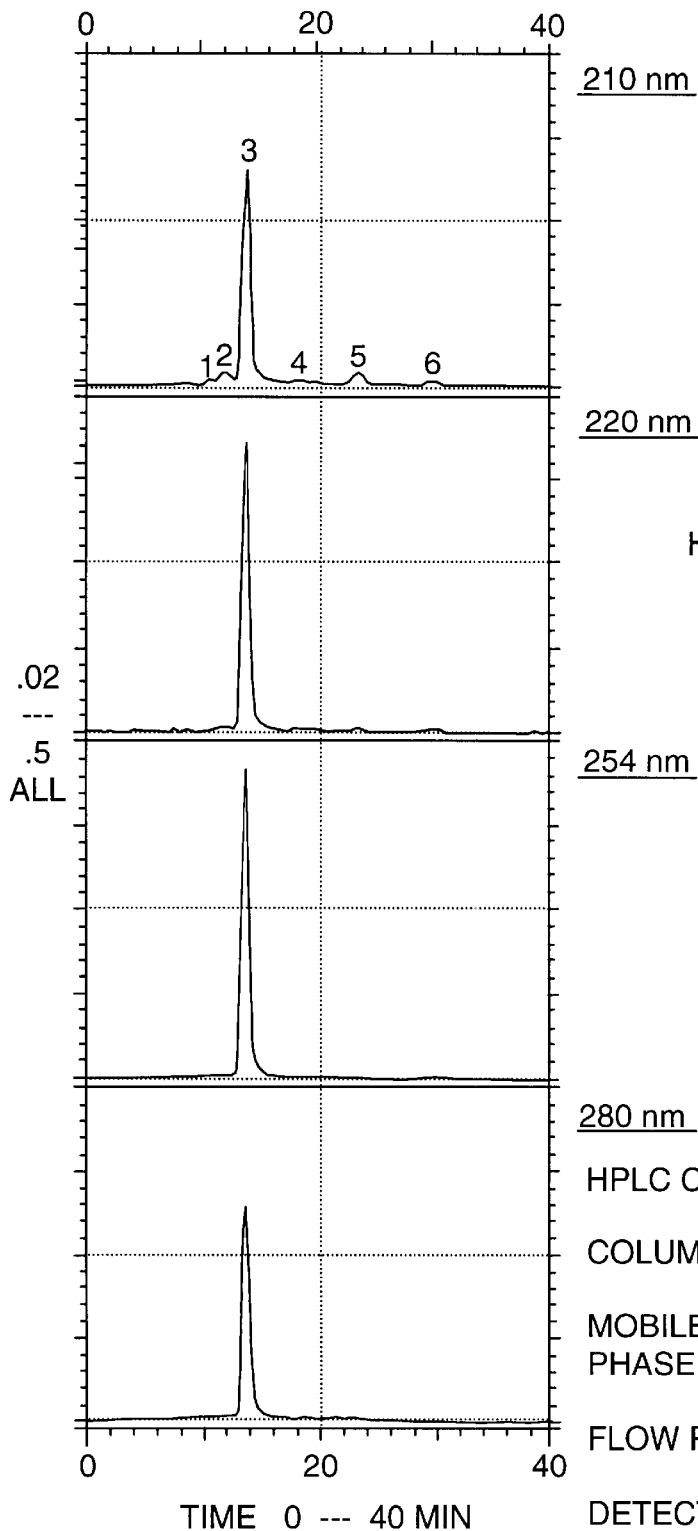
FIG. 3 is the HPLC chromatogram of ETM-SiOH-3 (ETM 305)
Figure 4:
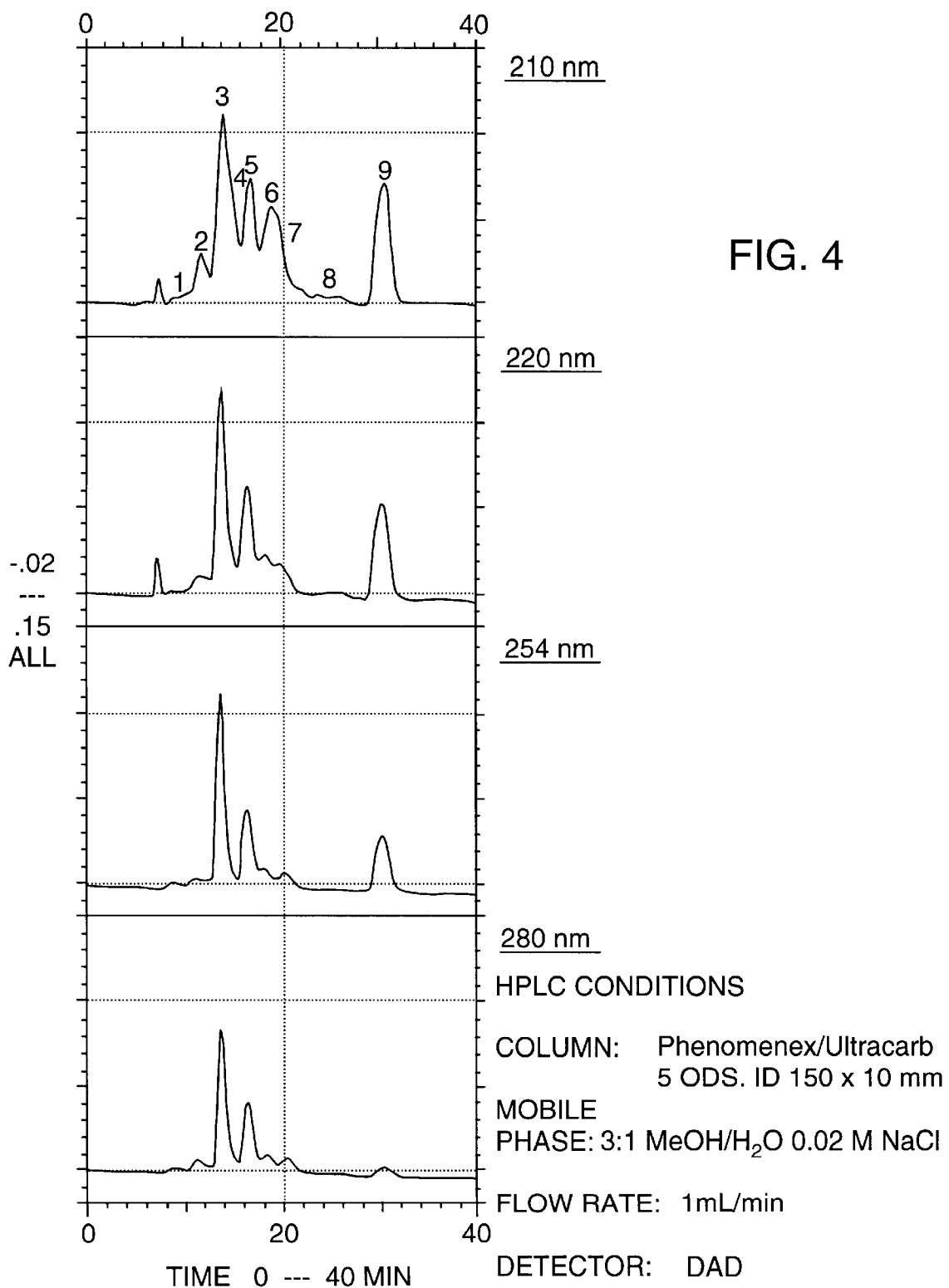
FIG. 4 is the HPLC chromatogram of ETM-SiOH-2 (trace metabolites)

The remaining cytotoxic fractions were further purified by HPLC (Phenomenex-Ultracarb ODS, 10 μm, 10×150 mm, 3:1 MeOH/H$_2$O 0.02 M NaCl, 1 mL/min., Da Detection: 210, 220, 254 and 280 nm). The most polar fraction (ETM-SiOH-4, 0.2 mg) yield 0. 1 mg of ETM 775 (FIG. 2). ETM-SiOH-3 yield 0.3 mg of ETM 305 (FIG. 3), and ETM-SiOH-2 consisted of a complex mixture of trace metabolites (FIG. 4).

TABLE 1

ETM-SiOH fractions: R$_f$, weight and cytoxic activity.

| ID # | Test tube # | R$_f$[a] | Weight | L1210 growth inhibition (%) at 500 ng/mL |
|---|---|---|---|---|
| ETM-SiOH 1 | 1 | 0.9 | 2.0 mg | 0 |
| ETM-SiOH 2 | 2 | 0.5, 0.7 | 0.3 mg | 80[b] |
| ETM-SiOH 3 | 4–5 | 0.5 | 0.4 mg | 30 |
| ETM-SiOH 4 | 6 | 0.3 | 0.2 mg | 3 |

[a]Silica gel TLC using 9:1 CHCl$_3$/MeOH as mobile phase.
[b]30% inhibition at 250 ng.

C. The Structure of ETM 305

Figure 5:
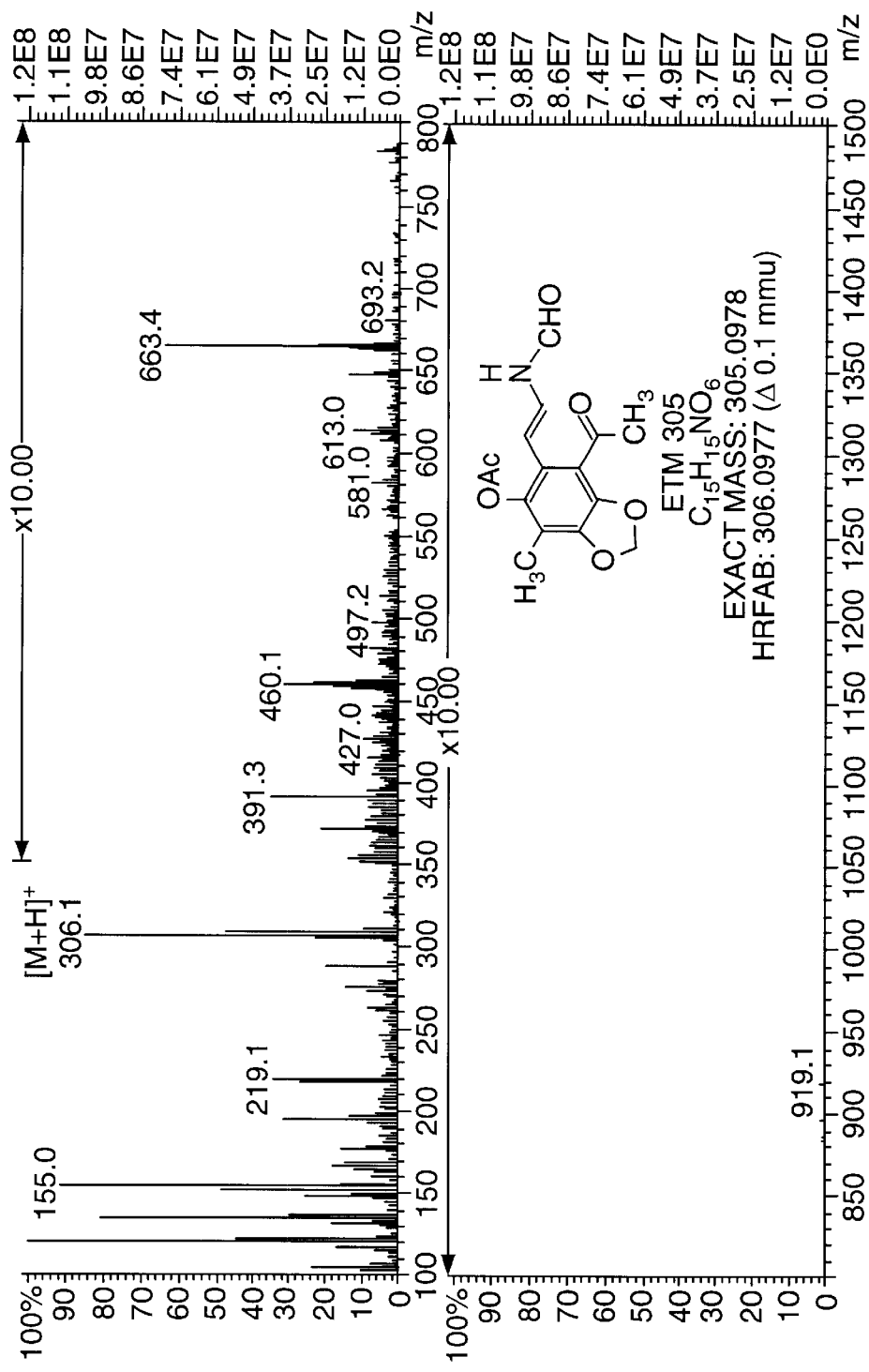
FIG. 5 is the LRFAB mass spectrum of ETM 305 in M.B. (magic bullet[4])
Figure 6:
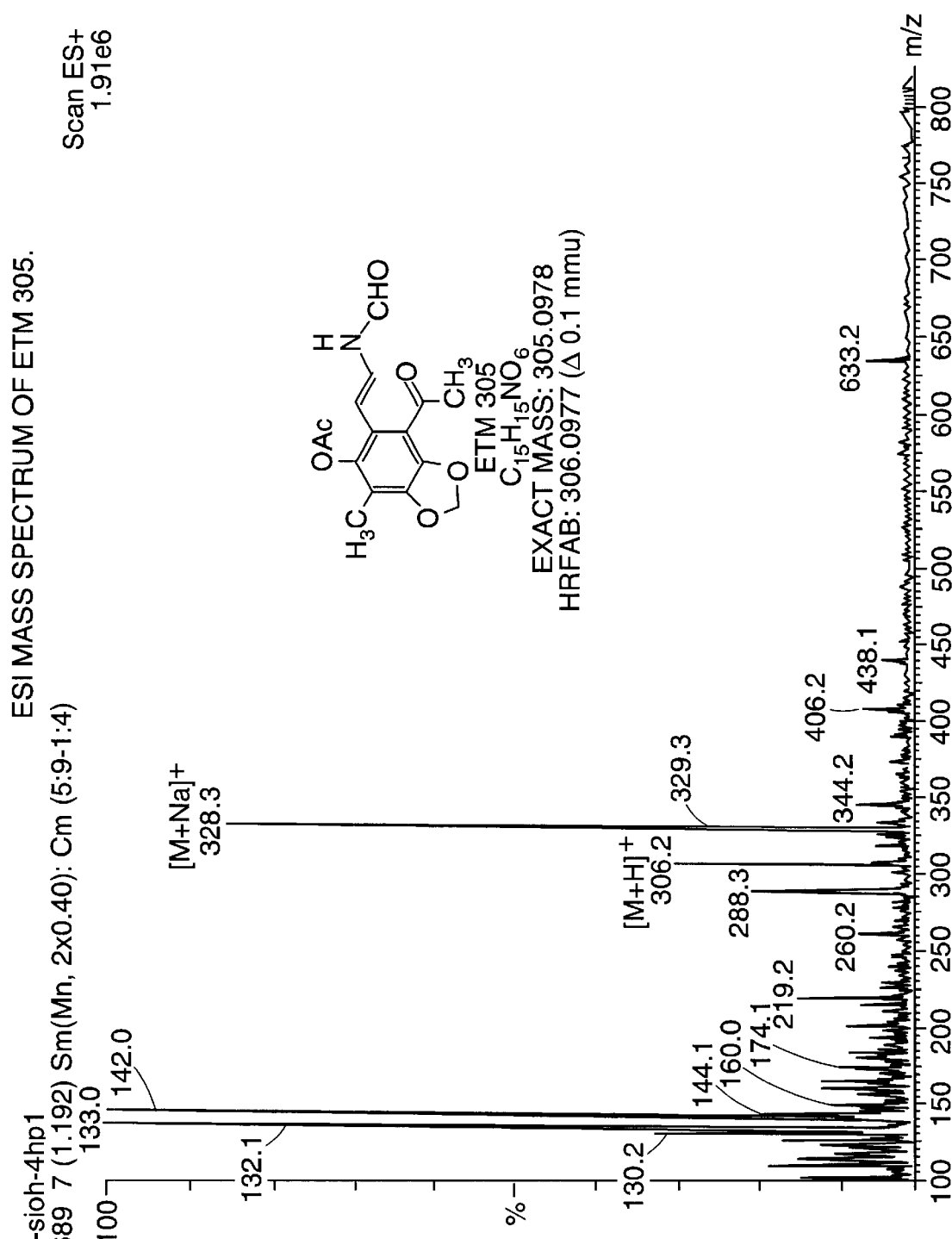
FIG. 6 is the ESI mass spectrum of ETM 305.
Figure 7:
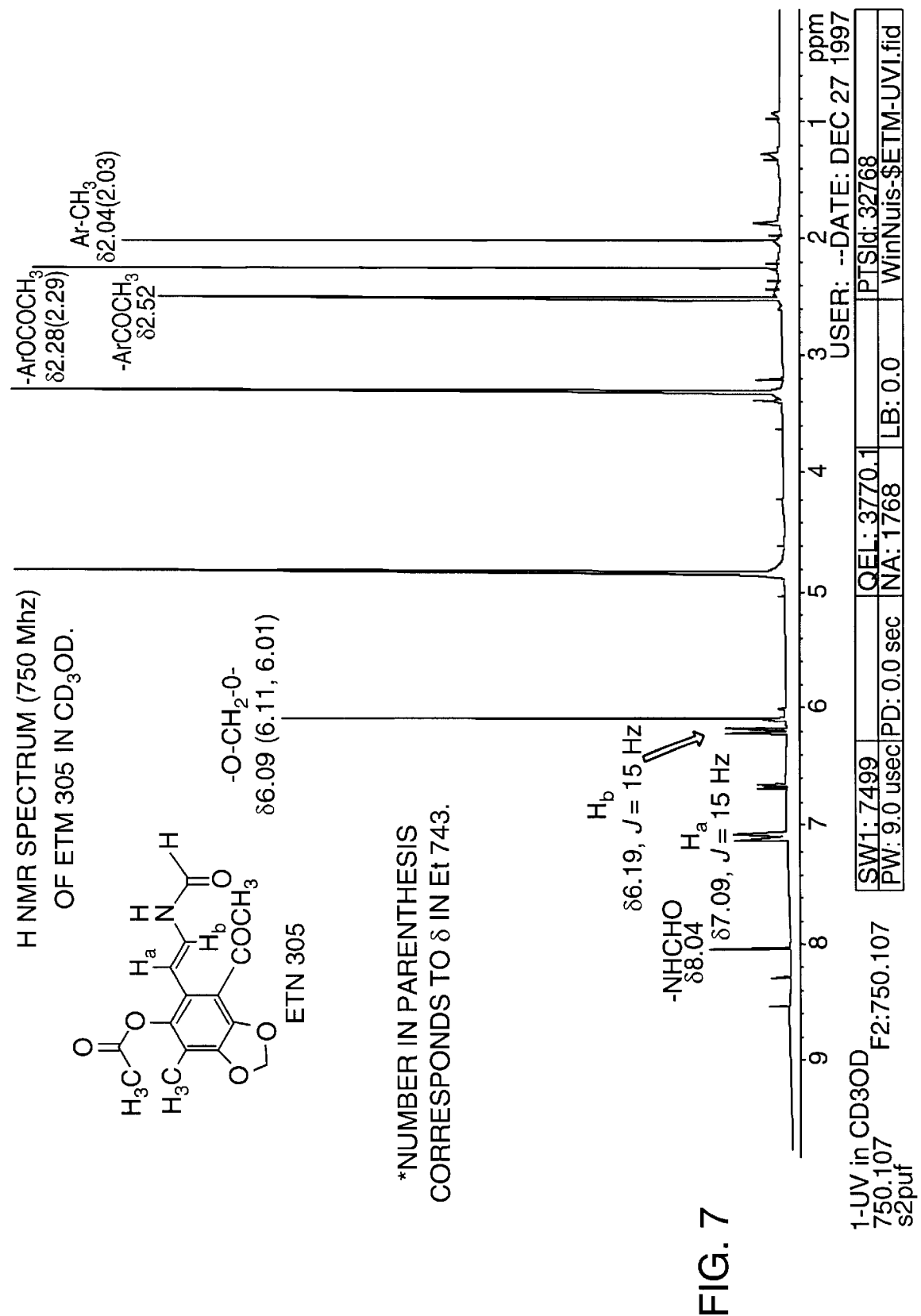
FIG. 7 is the $^1$H NMR spectrum (750 MHz) of ETM 305 in CD$_3$OD.

ETM 305 (IC$_{50}$ 0.2 μm/mL vs L1210 cells) showed a molecular ion at 306.0977 by HRFAB/MS (FIG. 5). This data is in agreement with the molecular formula C$_{15}$H$_{16}$NO$_6$ (Δ0.1 mmu). ESI/MS analysis confirmed the molecular weight of ETM 305 (FIG. 6); a molecular ion at m/z 306 was observed together with its sodium adduct (m/z 328). The $^1$H NMR spectrum of ETM 305 (FIG. 7) was very important for the structural assignment. Resonances at δ2.04, 2.28 and 6.09 were almost identical to those of Me-6 (δ2.03), —OCOCH$_3$ (δ2.29) and the dioxy-methylene protons (δ6.11 and 6.01) in Et 743,[1] respectively.

Figure 8:
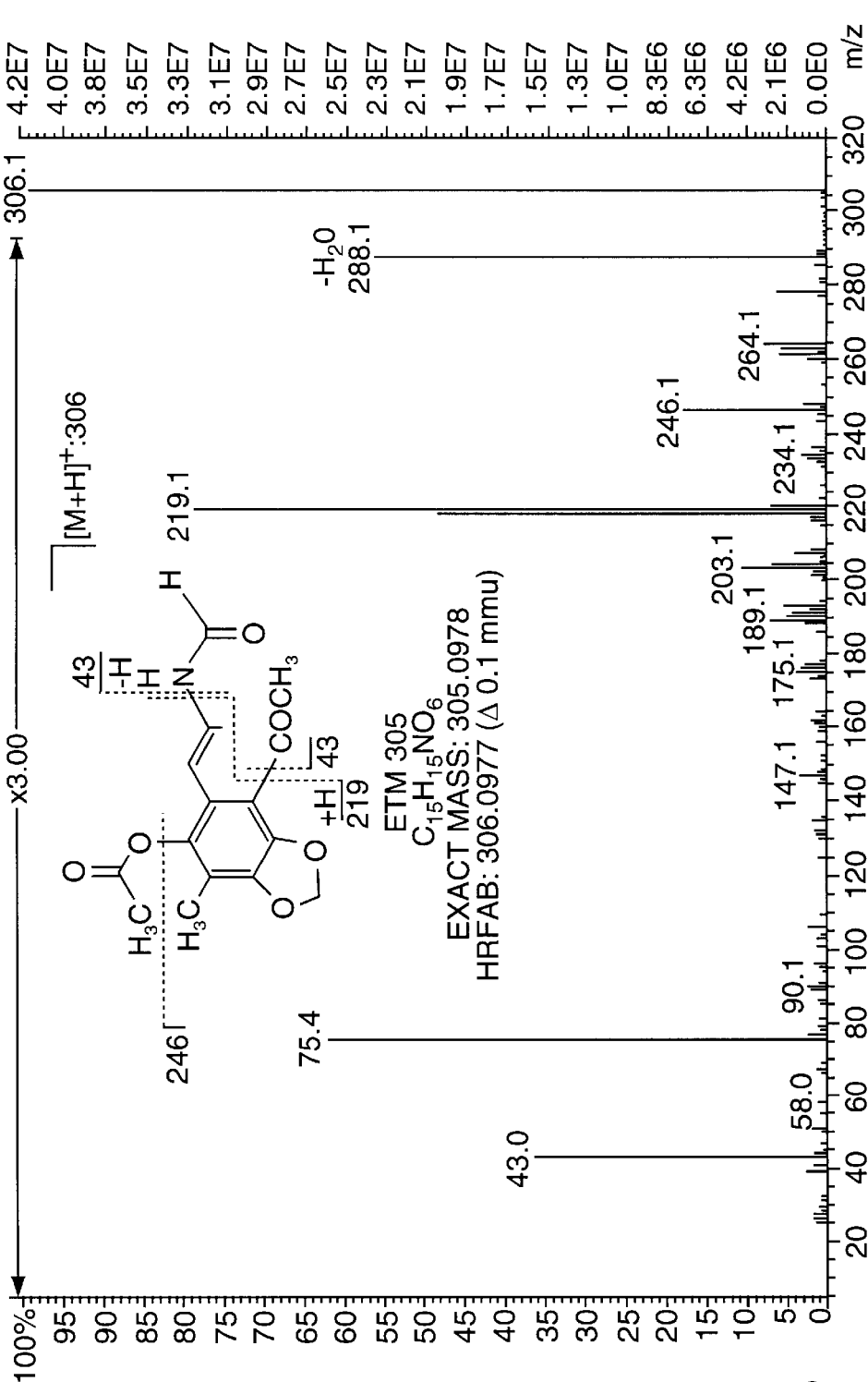
FIG. 8 is the FAB/MS/MS spectrum of ETM 305.
Figure 9:
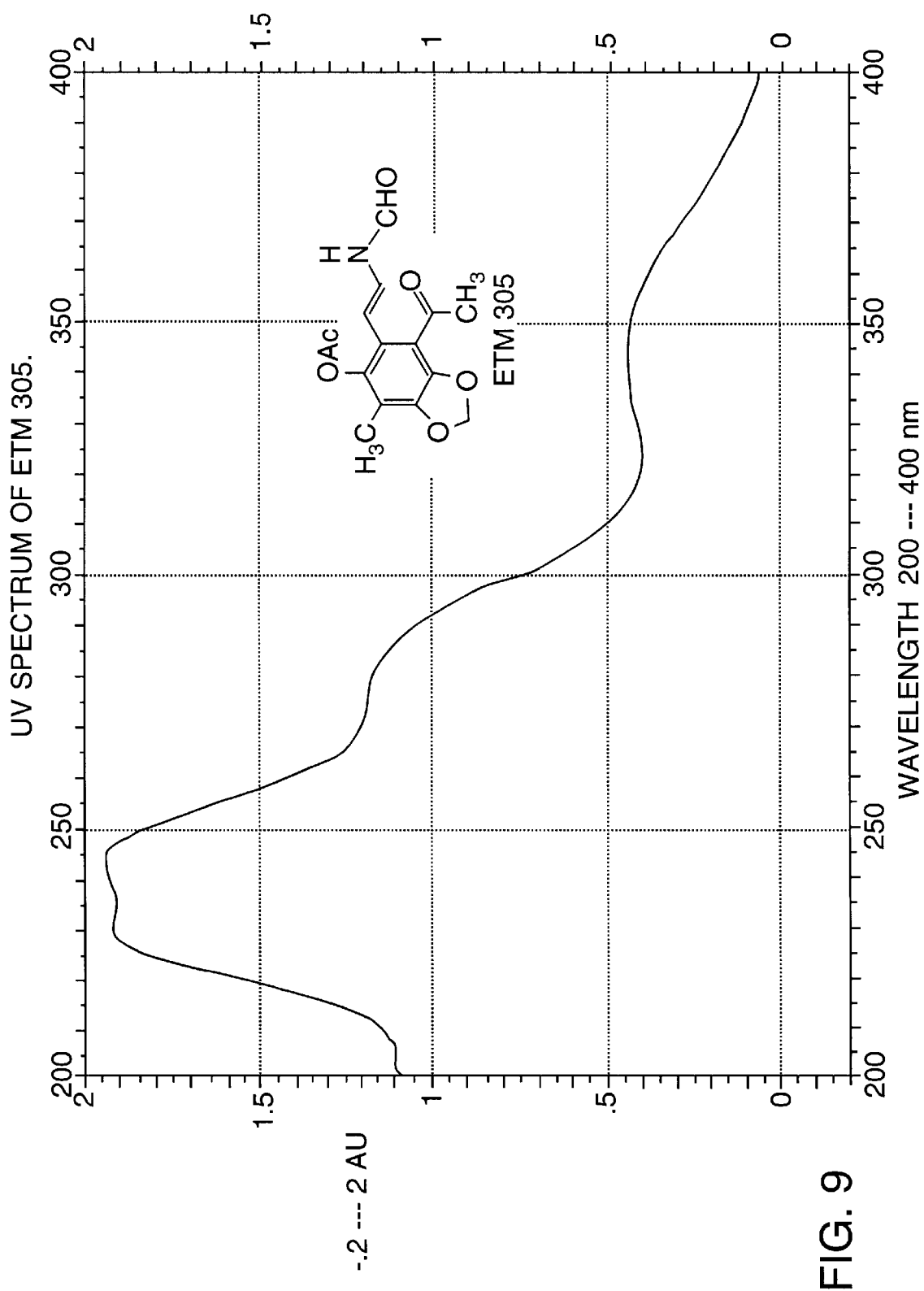
FIG. 9 is the UV spectrum of ETM 305.
Figure 10:
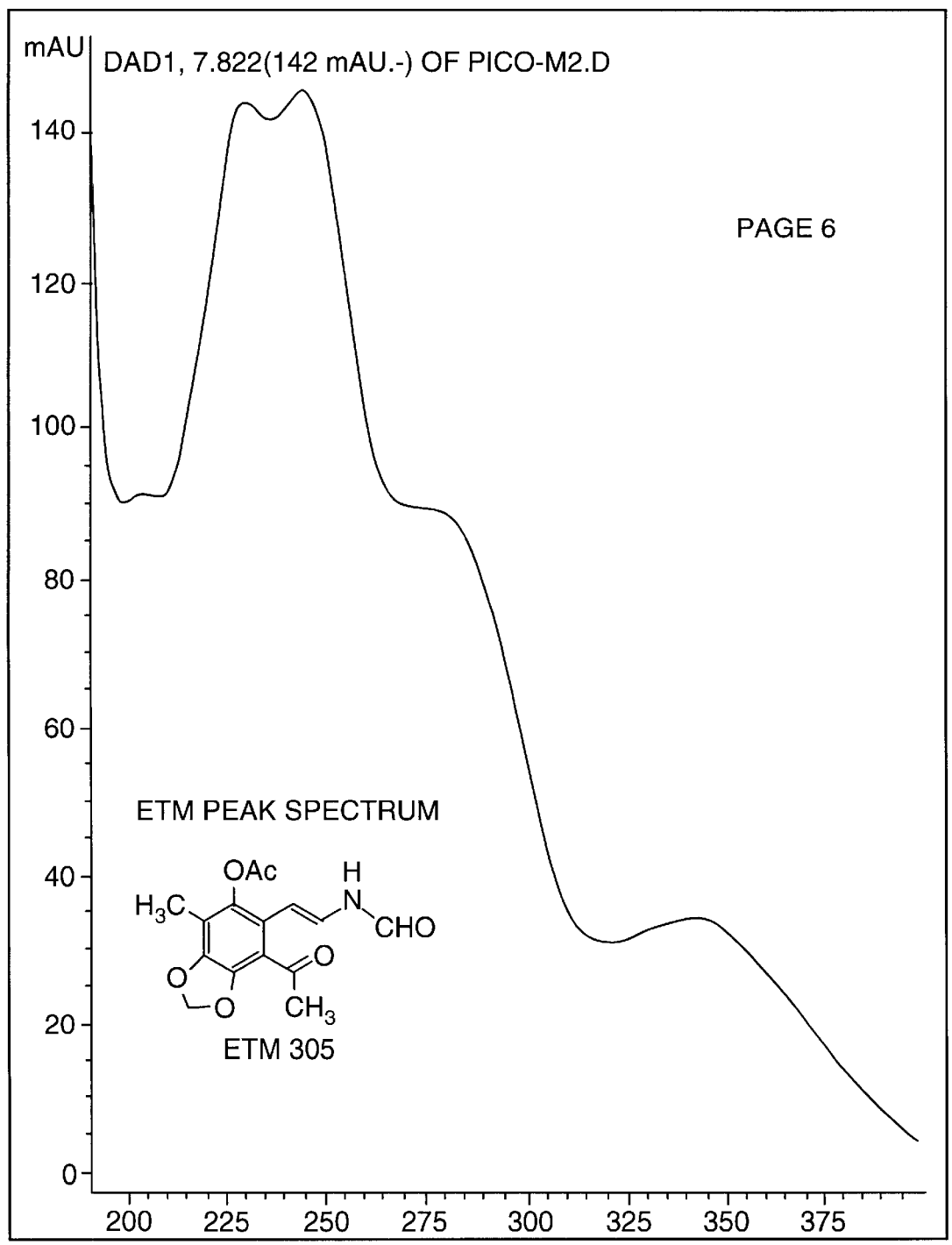
FIG. 10 is the UV spectrum of ETM.

In addition, it was observed resonances corresponding to a —CH═CH—NHCHO unit (δ7.09, d, 1H, J=15 Hz; δ6.19, d, 1H, J=15 Hz; δ8.04, s, 1H),[2] and an additional methyl group (δ2.52, s, 3H). The chemical shift of this methyl group match pretty well wit that of the methyl group on acetophenone[3] (δ2.55). It is interesting to note that the $^1$H NMR spectrum of ETM 305 consisted of two sets of resonances (4:1 ratio) due to rotational conformers around the —NH—CHO bond The $^1$H NMR data together with the MS data suggested that ETM 305 had the B-unit aromatic ring system of Et 743 attached to a vinyl-formamide unit and to a methyl ketone as shown in Scheme 1. FAB/MS/MS on m/z 306 supported the proposed structure (FIG. 8).

Scheme 1

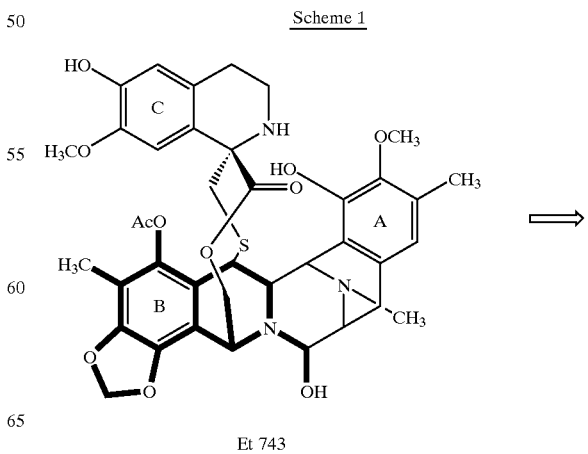

Et 743

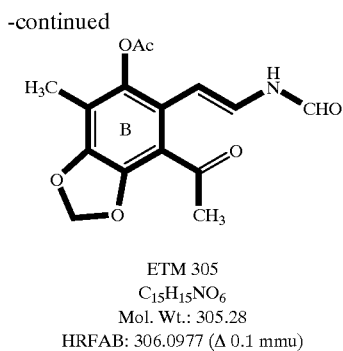

ETM 305
C₁₅H₁₅NO₆
Mol. Wt.: 305.28
HRFAB: 306.0977 (Δ 0.1 mmu)

D. The Structure of ETM 775

Figure 11:
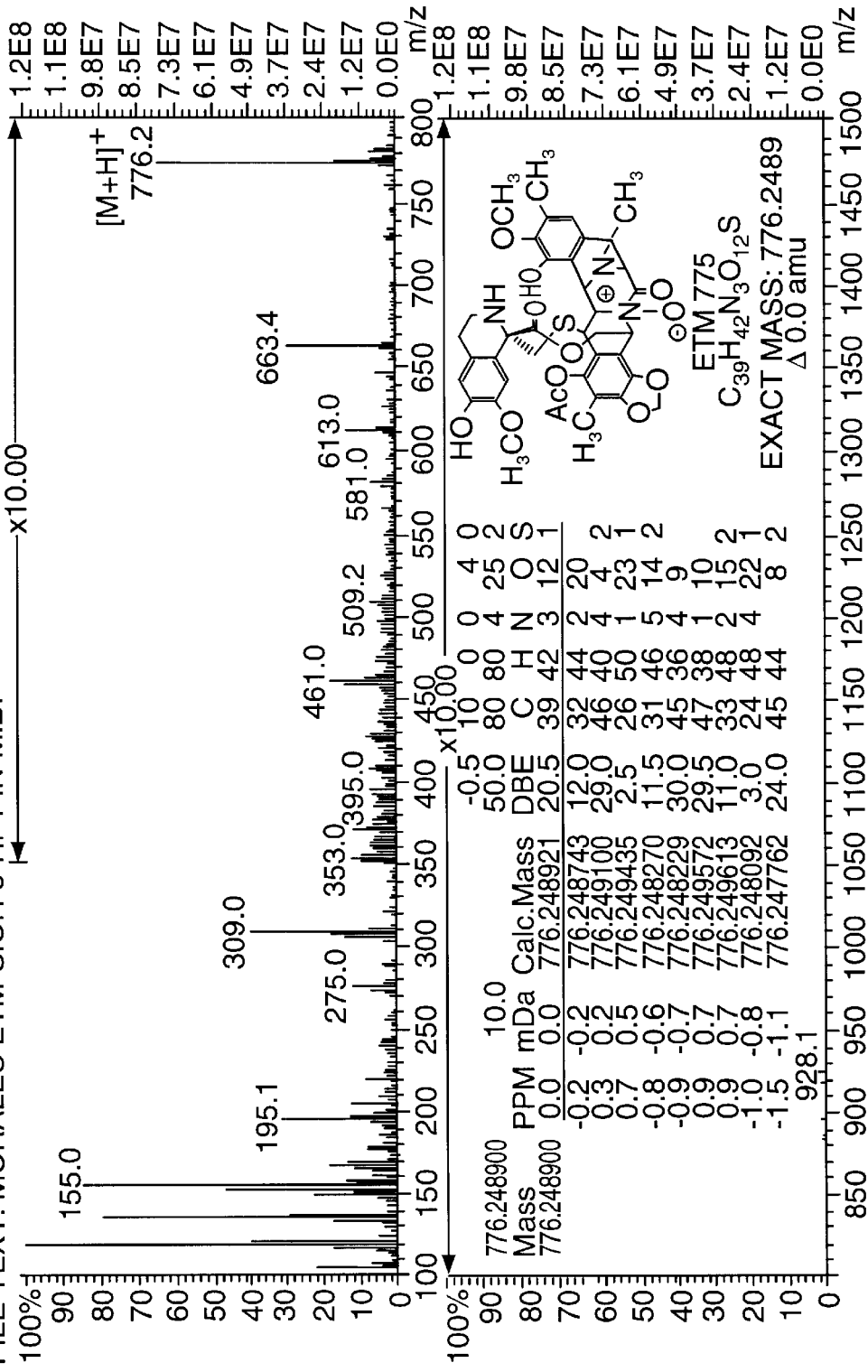
FIG. 11 is the LRFAB mass spectrum of ETM 775 in M.B.
Figure 12:
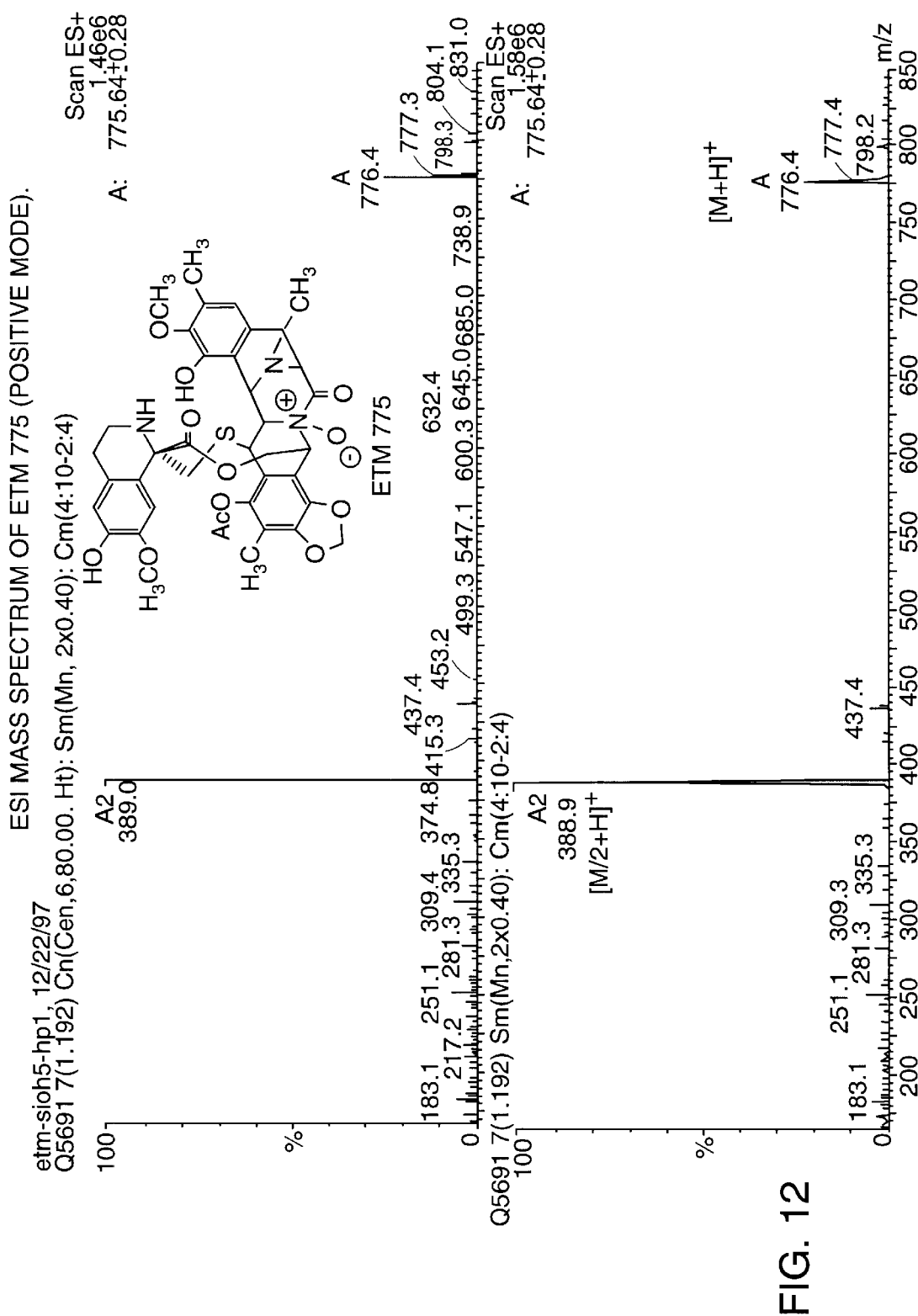
FIG. 12 is the ESI mass spectrum of ETM 775 (positive mode)
Figure 13:
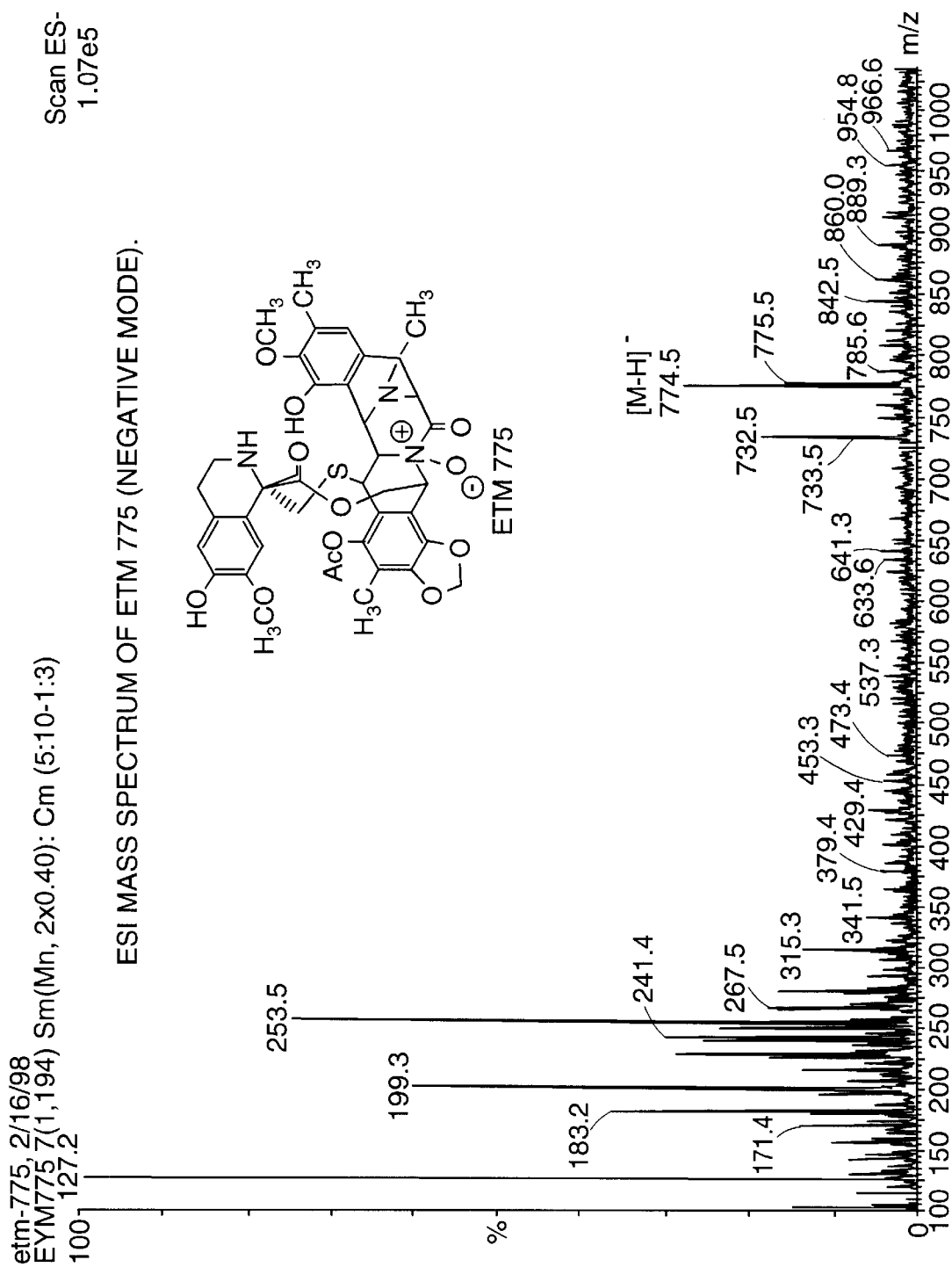
FIG. 13 is the ESI mass spectrum of ETM 775 (negative mode)
Figure 14:
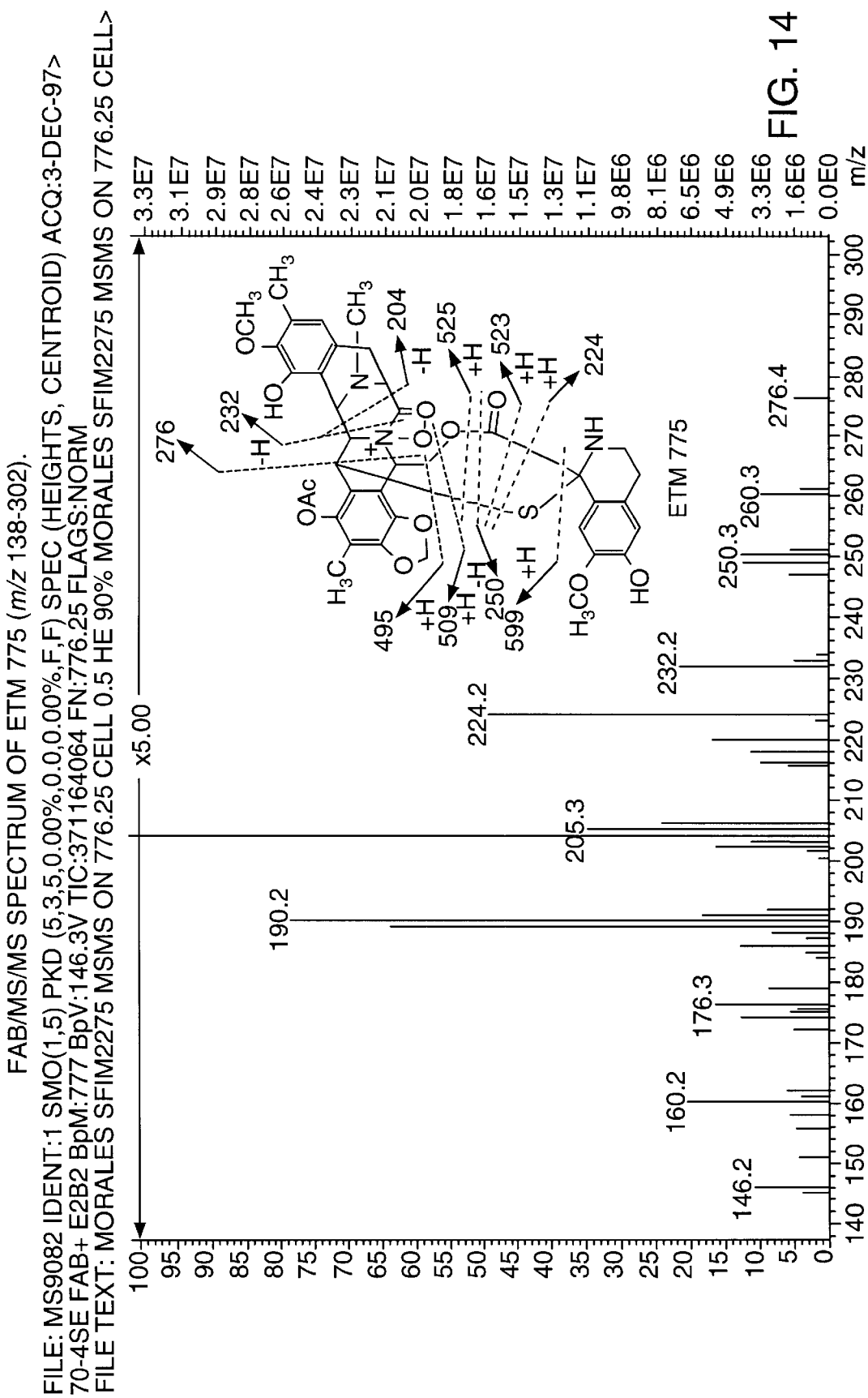
FIG. 14 is the FAB/MS/MS spectrum of ETM 775 (m/z 138–302)
Figure 15:
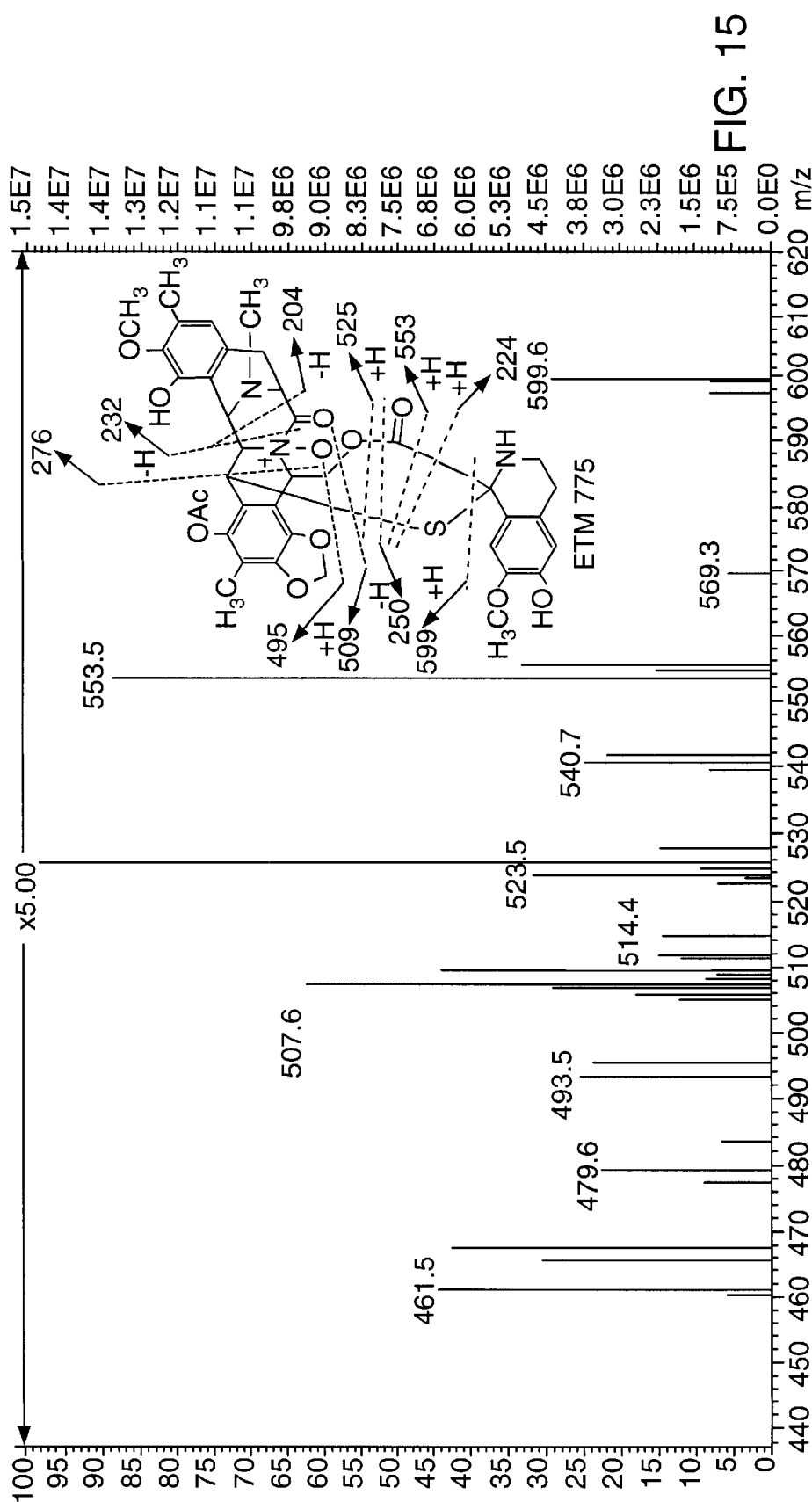
FIG. 15 is the FAB/MS/MS spectrum of ETM 775 (m/z 440–620)
Figure 16:
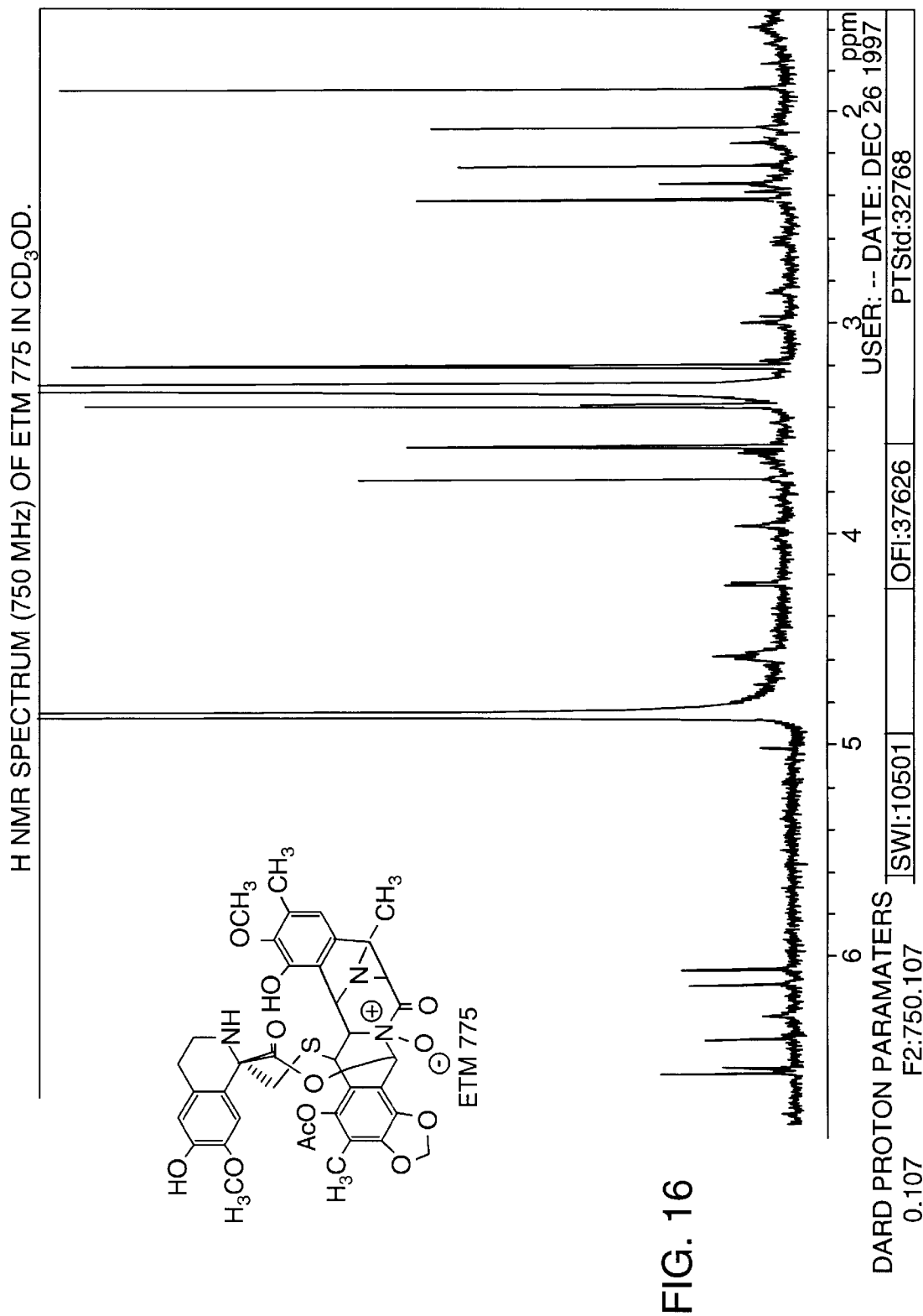
FIG. 16 is the $^1$H NMR spectrum (750 MHz) of ETM 775 in CD$_3$OD.
Figure 17:
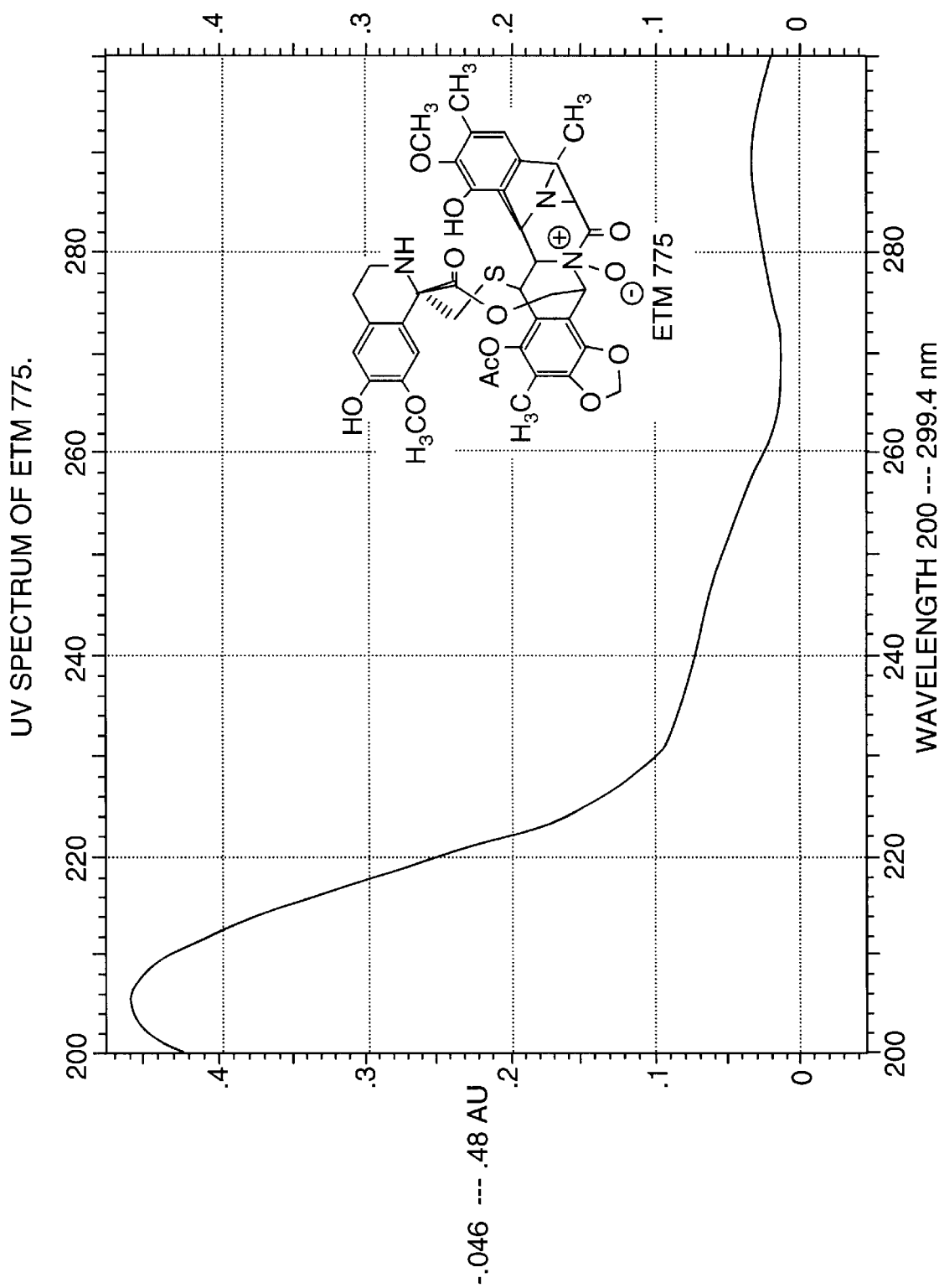
FIG. 17 is the UV spectrum of ETM 775.

ETM 775 ($IC_{50}$ 0.2 μg/mL vs L1210 cells) showed a molecular ion at 776.2489 by HRPAB/MS FIG. 11). This data is in agreement with the molecular formula $C_{39}H_{42}N_3O_{12}S$ (Δ0.0 mmu) which indicated that ETM 775 is an oxidation product of Et 743. Both, positive and negative mode ESI/MS spectra confirmed the molecular weight of ETM 775 (FIGS. 12 and 13). Because of the limited amount of ETM 775, the structural assignment was carried out mainly by interpretation of its mass spectral data. FABMS/MS on M+H of ETM 775 (m/z 776) was critical in assigning the location of the extra oxygen was located on N-2 in the form of an N-oxide as revealed by peaks at m/z 276 and 260 (276-oxygen). A fragment ion at m/z 232, not observed in Et 743, suggested that the carbinol amine oxygen was oxidized to the amide (Scheme 3). The structures of the A- and C-units in ETM 775 remained intact as revealed by the presence of the characteristic mass spectral peaks at m/z 204 (A-unit), and m/z 224 and 250 (C-unit).[1] Both, the 750 750 Mhz ¹H NMR (FIG. 16) and the UV (FIG. 17) spectra resembled those of Et 743.[1]

Scheme 2

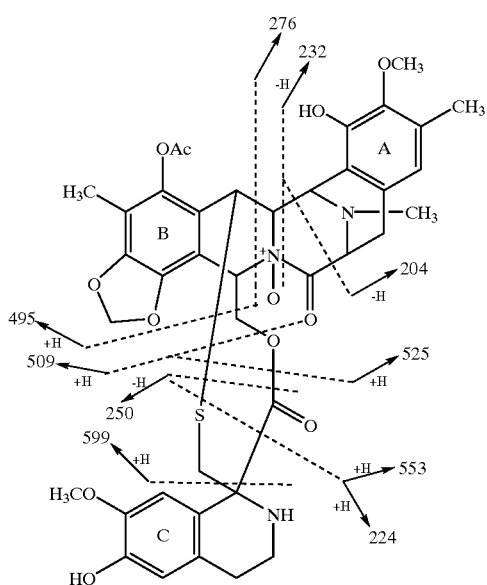

ETM 775
C₃₉H₄₂N₃O₁₂S
HRFAB: 776.2489 (Δ 0.0 amu)

II. Et 743—Mayo Metabolic Study
A. M1 metabolite (ETM 305)

Figure 18:
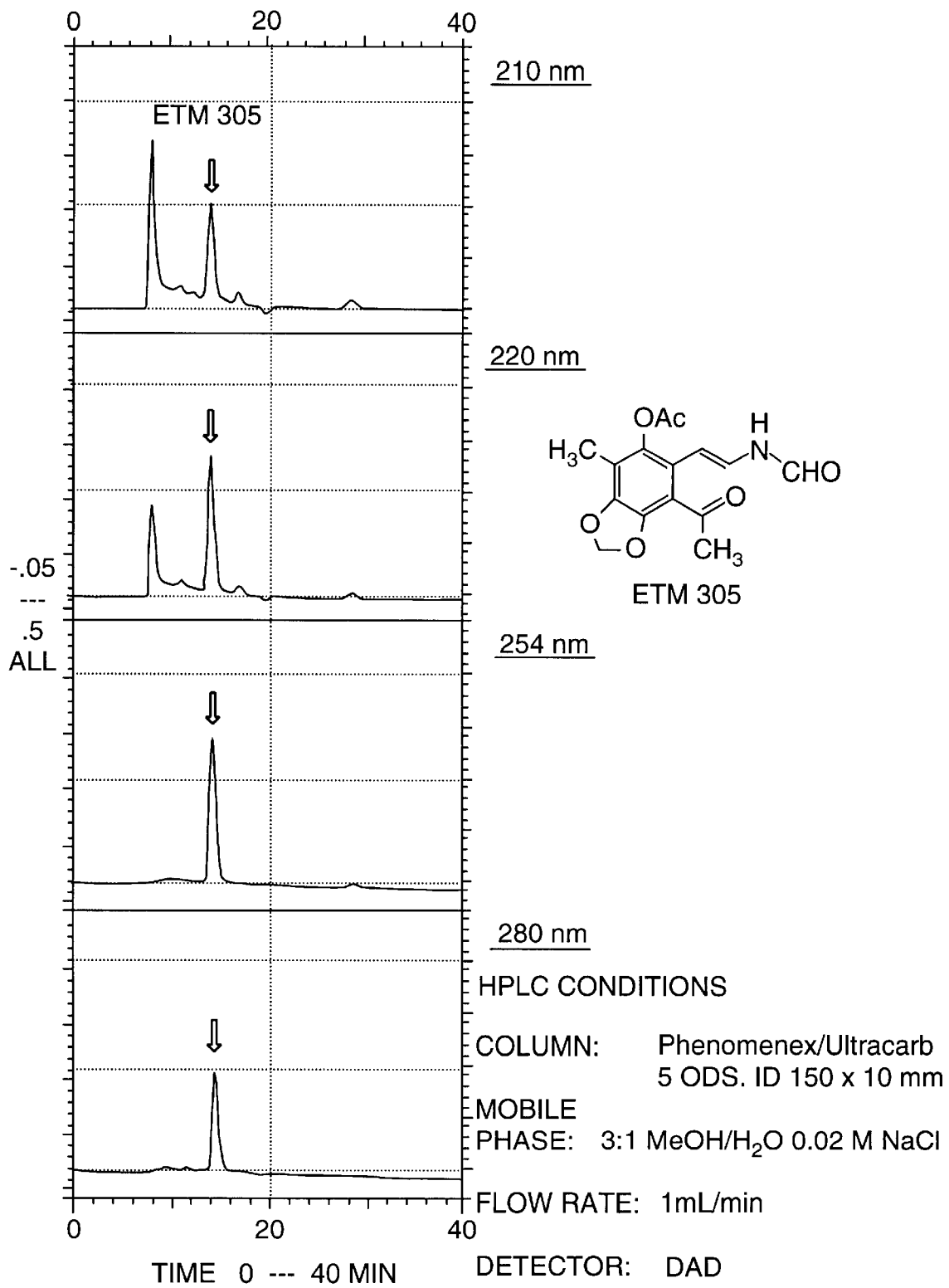
FIG. 18 is the HPLC choromatogram of ETM 305.
Figure 19:
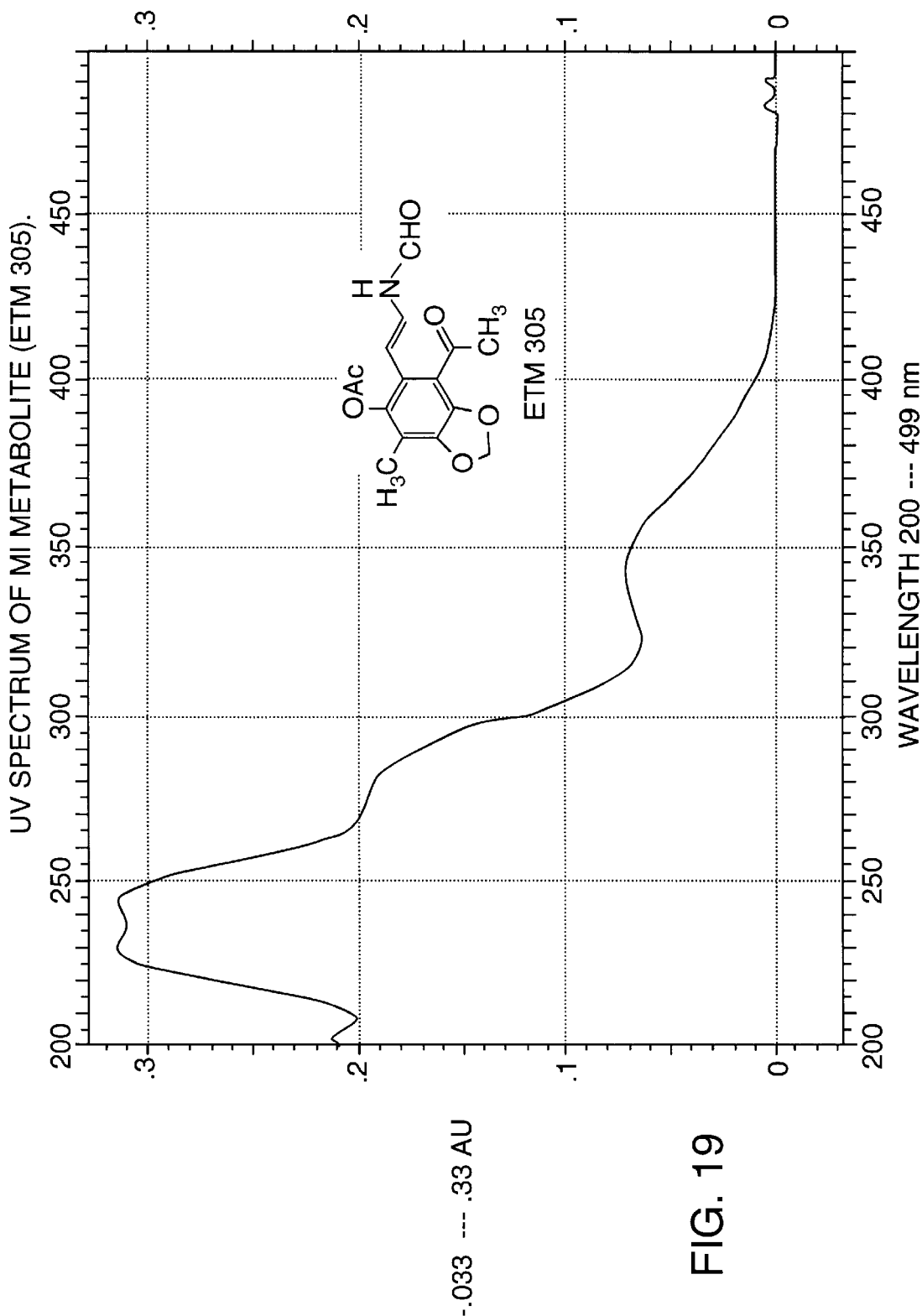
FIG. 19 is the UV spectrum of ETM 305.
Figure 20:
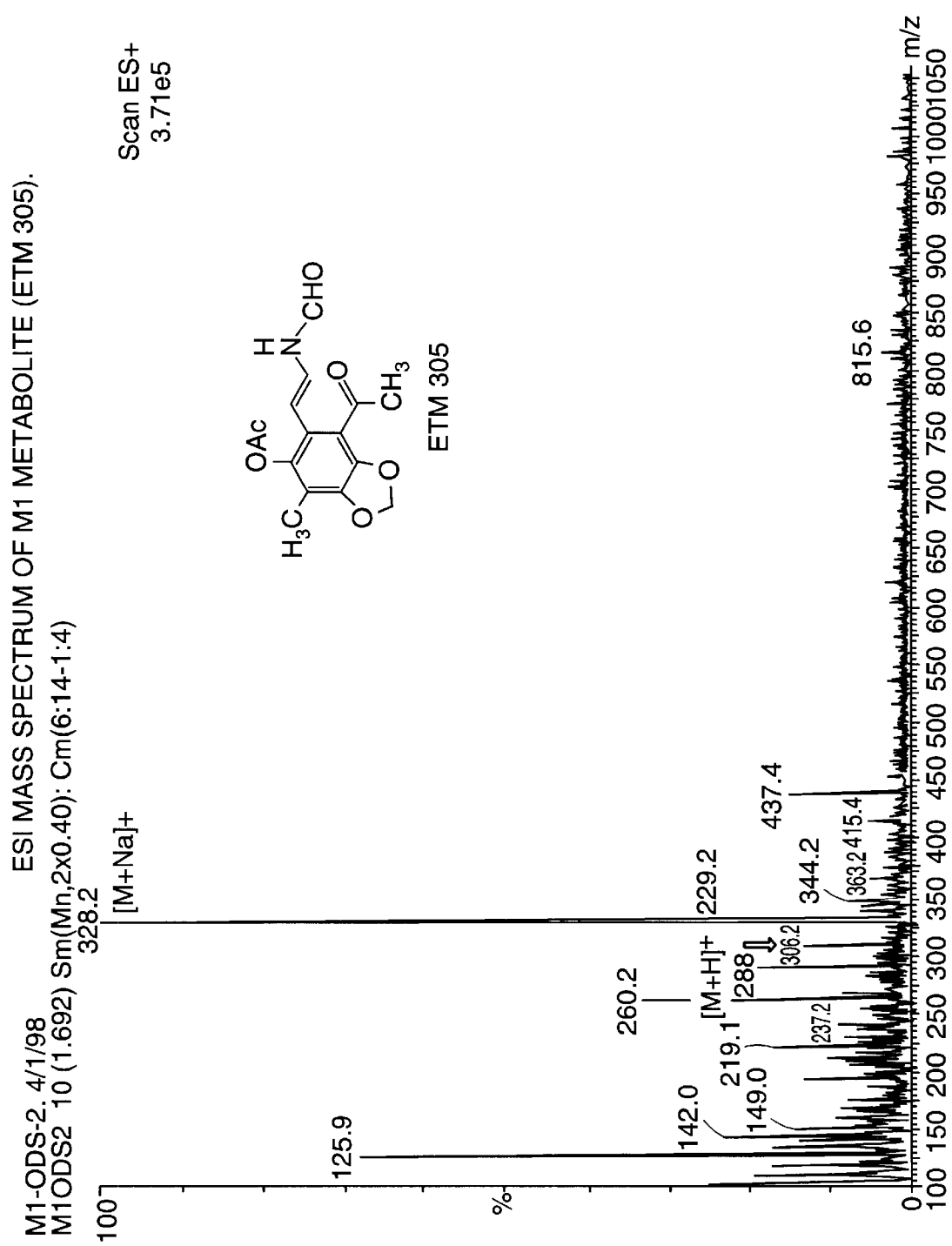
FIG. 20 is the ESI mass spectrum of ETM 305.

The ETM sample was filtered through a C18 sep-pack and the eluant (3:1 MeOH/H₂O) concentrated under a nitrogen stream. Purification of the resulting residue by HPLC (same conditions as described above) revealed the presence of a compound with a retention time identical to that of ETM 305 (FIG. 18). Both, the UV (FIG. 19) and ESI/MS (FIG. 20) spectra of M1 were identical to that of ETM 305. Thus, it was concluded that M1 metabolite had the same chemical structure as ETM 305.

B. M2 metabolite (ETM 204)

The provided sample was filtered through a C18 sep-pack and the eluant (3:1 MeOH/H₂O) concentrated under a nitrogen stream and the resulting residue analyzed by FAB/MS, ESI/MS and ¹H NMR.

C. The Structure of ETM 204 (M2)

Figure 21:
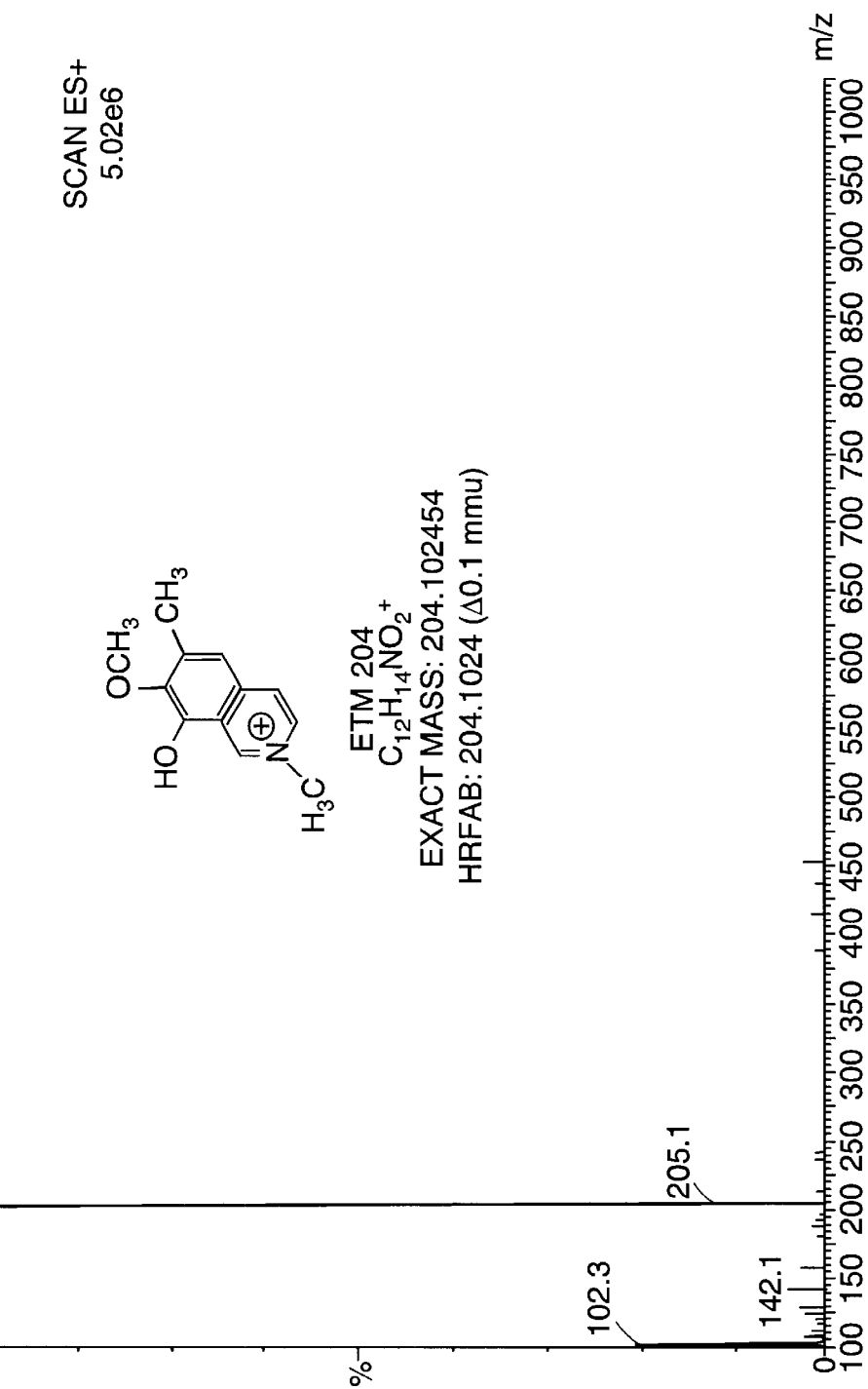
FIG. 21 is the ESI mass spectrum of ETM 204.

ETM 204 showed a molecular ion at 204.1024 by HRFAB/MS. This data is in agreement with the molecular formula $C_{12}H_{14}NO_2$ (Δ0.0 mmu). ESI/MS analysis confirmed the molecular weight as 204 (FIG. 21). The molecular formula matched with the molecular formula of the a-unit in Et 743. Thus, the chemical structure of ETM 204 was proposed to be the aromatic ammonium salt derivative shown in Scheme 3. This simple compound (as well as the other metabolites) can easily be monitored to assay the breakdown of Et 743 in vivo.

Scheme 3

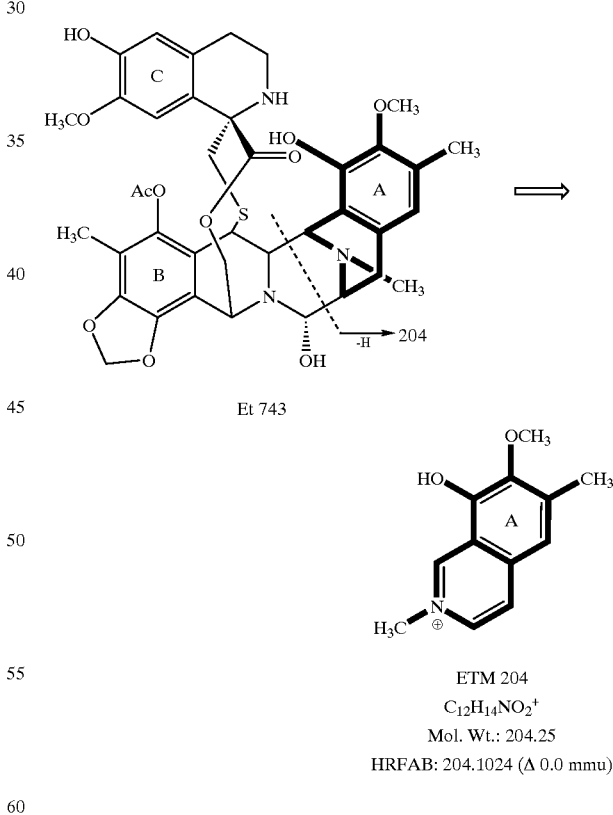

ETM 204
C₁₂H₁₄NO₂⁺
Mol. Wt.: 204.25
HRFAB: 204.1024 (Δ 0.0 mmu)

Figure 22B:
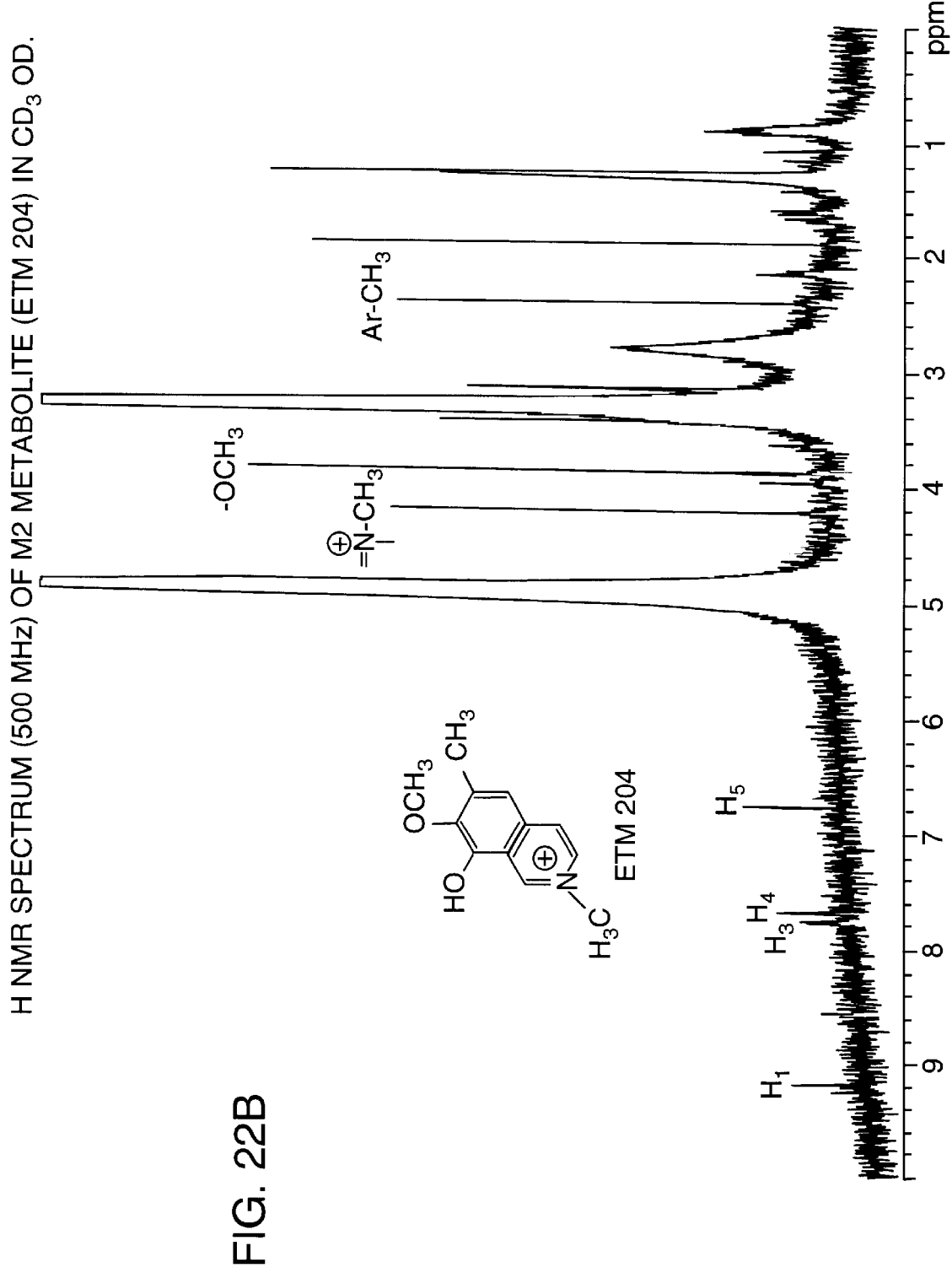
FIG. 22 is the $^1$H NMR spectrum (500 MHz) of ETM 204 in CD$_3$OD.
Figure 23:
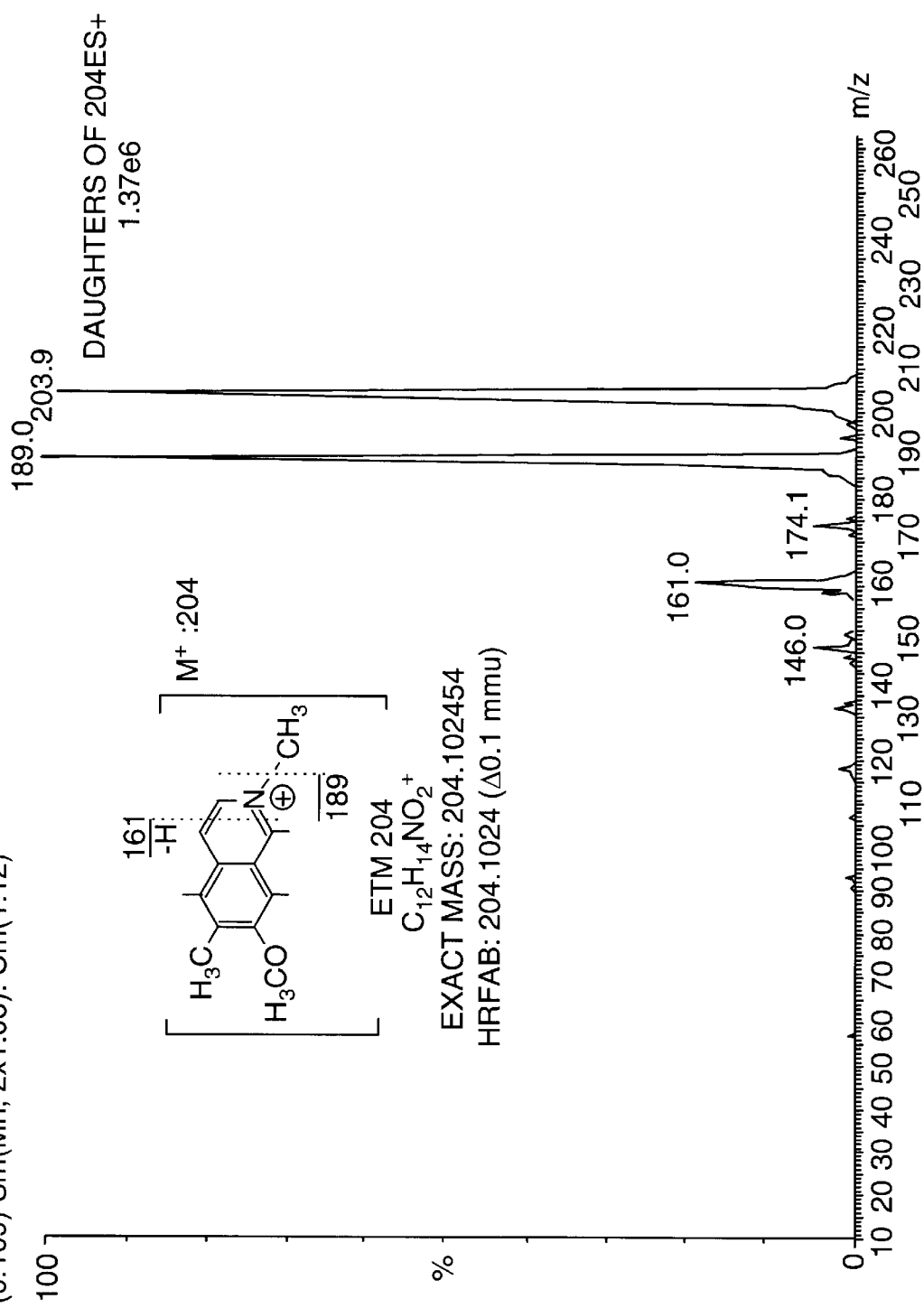
FIG. 23 is the ESI/MS/MS spectrum of ETM 204.

A ¹H NMR spectrum (FIG. 22) of ETM 204 showed resonances that supported the proposed structure: four aromatics signals (δ9.2, s; δ7.8, d, J=5 Hz, and 6 6.8, s) and three methyl singlets (δ4.2, δ3.9 and δ2.4) The ESI/MS/MS of ETM 204 (FIG. 23) showed a prominent peak ion at 189 corresponding to the apparent loss of the N-methyl group (204—CH₃).

Biological Studies of ETM-305 and ETM-775

Compounds ETM-305 and ETM-775 have been assayed employing standard protocols for the following tumor cell lines; P-388 (murine leukemia); A-549 (human lung carcinoma); HT-29 (human colon adenocarcinoma); and MEL-28 (human malignant melanoma). See, for example, Bergeron et al., *Biochem. Biophys. Res. Comm.,* 1984, 121 (3) 848–854 and Schroeder et al., *J. Med. Chem.,* 1981, 24 1078–1083. These results are shown below in Table 2:

TABLE 2

| | Cell Line & Activity $IC_{50}$ ($\mu$g/ml) | | | |
|---|---|---|---|---|
| | Compound: | | | |
| | P-388 | A-549 | HT-29 | MEL-28 |
| ETM-305 | 0.5 | 0.5 | 0.5 | 0.25 |
| ETM-775 | 0.01 | 0.01 | 0.01 | 0.01 |

Methods of Treatment

The present invention includes bioactive compounds, and accordingly, an embodiment of the present invention is directed to methods of treatment using such compounds. As described above, the compounds of the present invention have exhibited in vitro cytoxicity against tumor cell lines. It is anticipated that these in vitro activities will likewise extend to in vivo utility.

These compounds have been isolated in substantially pure form, i.e., at a purity level sufficient to allow physical and biological characterization thereof. These compounds have been found to possess specific antitumor activities and as such they will be useful as medicinal agents in mammals, particularly in humans. thus, another aspect of the present invention concerns pharmaceutical compositions containing the active compounds identified herein and methods of treatment employment such pharmaceutical compositions.

As described above, the active compounds of the present invention exhibit antitumor activity, thus, the present invention also provides a method of treating any mammal affected by a malignant tumor sensitive to these compounds, which comprises administering to the affected individual a therapeutically effective amount of an active compound or mixture of compounds, or pharmaceutical compositions thereof. The present invention also relates to pharmaceutical preparations, which contain as active ingredient one or more of the compounds of this invention, as well as the processes for its preparation.

Example of pharmaceutical compositions include any solid (tablets, pills, capsules, granules, etc.) or liquid (solutions, suspensions of emulsions) with suitable composition or oral, topical or parenteral administration, and they may contained the pure compound or in combination with any carrier of other pharmacologically active compounds. These compositions may need to be sterile when administered parenterally.

The terms "unit dose" as it pertains to the present invention refers to physically discrete units suitable as unitary dosages for animals, each unit containing a predetermined quantity of active material calculated to produce the desired antitumor effect in association with the required diluent; i.e., carrier, or vehicle. The specifications for the novel unit dose of this invention are dictated by and are directly dependent on (a) the unique characteristics of the active material and the particular antitumor effect to be achieved, and (b) the limitations inherent in the art of compounding such active material for antitumor use in animals.

Unit dosage forms are typically prepared from the frozen or dried active compound (or salts thereof) by dispersement in a physiologically tolerable (i.e., acceptable) diluent or vehicle such as water, saline or phosphate-buffered saline to form an aqueous composition. Such diluents are well known in the art and are discussed, for example, in Remington's Pharmaceutical Sciences, 16th Ed., Mack Publishing Company, Easton, Pa. (1980) at pages 1465–1467.

Dosage forms can also include an adjuvant as part of the diluent. Adjuvants such as complete Freund's adjuvant (CFA), incomplete Freund's adjuvant (IFA) and alum are materials well known in the art, and are available commercially from several sources.

The quantity of active compound to be administered depends, inter alia, on the animal species to be treated, the subject animal's size, the size of the tumor (if known), the type of tumor (e.g., solid) present, and the capacity of the subject to utilize the active compound. Precise amounts of active compound required to be administered depend on the judgment of the practitioner and are peculiar to each individual, particularly where humans are the treated animals. Dosage ranges, however, can be characterized by a therapeutically effective blood concentration and can range from a concentration of from about 0.01 $\mu$M to about 100 $\mu$M, preferably about 0.1 $\mu$M to 10 $\mu$M.

Suitable regimes for initial administration and booster injections are also variable, but are typified by an initial administration followed by repeated doses at one or more hour intervals by a subsequent injection or other administration. Alternatively, continuous intravenous infusion sufficient to maintain a therapeutically effective concentration in the blood are contemplated.

REFERENCES

The following background references are provided to assist the reader in understanding this invention. To the extent necessary, the contents are hereby incorporated herein by reference.

1. A) Rinehart et al., *J. Org. Chem.* 1990, 55, 4512. B) Rinehart et al., *J. Am. Chem. Soc.,* 1996, 118 9017.
2. Herbert et al., *J. Chem. Soc. Perkin Trans. I,* 1987, 1593.
3. Pretsch et al. *Tables of Spectral Data for Structure Determination of Organic Compounds;* Springer-Verla: Berlin, 1989; p. H125.
4. Rinehart et al., *Biochem. Res. Commun.,* 1984, 124, 350.

The present invention has been described in detail, including the preferred embodiments thereof However, it will be appreciated that those skilled in the art, upon consideration of the present disclosure, may make modifications and/or improvements on this invention and still be within the scope and spirit of this invention.

What is claimed is:
1. Substantially pure ETM-775 having the following structure:
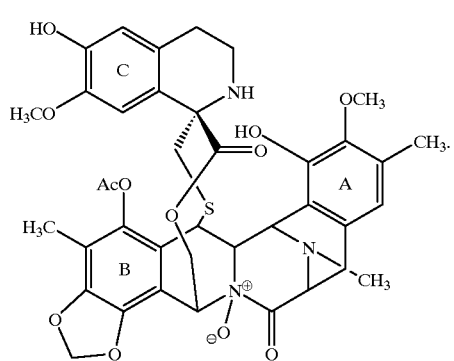
ETM 775
2. A pharmaceutical composition comprising ETM-775 and a pharmaceutically acceptable carrier, diluent or excipient.
* * * * *